United States Patent
Ishii et al.

(10) Patent No.: US 11,967,415 B2
(45) Date of Patent: Apr. 23, 2024

(54) EXCREMENT JUDGEMENT SYSTEM, EXCREMENT JUDGEMENT METHOD, AND EXCREMENT JUDGEMENT DEVICE

(71) Applicant: TOTO LTD., Kitakyushu (JP)

(72) Inventors: Katsunori Ishii, Fukuoka (JP); Mayu Okubo, Fukuoka (JP)

(73) Assignee: TOTO LTD., Kitakyushu (JP)

(*) Notice: Subject to any disclaimer, the term of this patent is extended or adjusted under 35 U.S.C. 154(b) by 0 days.

(21) Appl. No.: 17/681,933

(22) Filed: Feb. 28, 2022

(65) Prior Publication Data

US 2023/0274815 A1 Aug. 31, 2023

(51) Int. Cl.
*G16H 30/40* (2018.01)
*G06T 7/00* (2017.01)
*G16H 50/30* (2018.01)

(52) U.S. Cl.
CPC ........... *G16H 30/40* (2018.01); *G06T 7/0002* (2013.01)

(58) Field of Classification Search
USPC ......................................... 382/128
See application file for complete search history.

(56) References Cited

U.S. PATENT DOCUMENTS

| 2018/0368818 | A1 | 12/2018 | Oguri et al. | |
| 2022/0178126 | A1* | 6/2022 | Azuma | A61B 10/0038 |
| 2022/0375080 | A1* | 11/2022 | Aoyama | G06V 10/62 |

FOREIGN PATENT DOCUMENTS

| EP | 4036334 A1 * | 8/2022 | ........... G06T 7/0012 |
| JP | 6742663 | 8/2020 | |
| JP | 2021-050983 | 4/2021 | |
| JP | 2021-051449 | 4/2021 | |
| WO | WO-2021024584 A1 * | 2/2021 | |
| WO | 2021/060174 | 4/2021 | |
| WO | WO-2021060174 A1 * | 4/2021 | ........... G06T 7/0012 |
| WO | WO-2021192476 A1 * | 9/2021 | |

OTHER PUBLICATIONS

Ohno et al., Validity of an observational assessment tool for multifaceted evaluation of faecal condition, 2019,9:37601 https://doi.org/10.1038/s41598-019-40178-5, pp. 1-9. (Year: 2019).*

Choy et al., Detection and Classification of Human Using Deep Convolution Neural Networks, IEEE Access, Dec. 2021, IEEE Engineering in Medicine and Biology Society section, vol. 9. 2021, pp. 160485-160496. (Year: 2021).*

* cited by examiner

*Primary Examiner* — Ishrat I Sherali
(74) *Attorney, Agent, or Firm* — Amin, Turocy & Watson, LLP

(57) ABSTRACT

An excrement judgement system according to the embodiment including: an acquisition unit that acquires image information on an image in which excrement excreted in a defecation action per time is captured; a determination unit that determines properties of a plurality of stools included in the image information and stool amounts corresponding to the properties of the plurality of stools; and an outputting unit that associates the properties of the plurality of stools and the stool amounts corresponding to the properties of the plurality of stools that are determined by the determination unit, and outputs the associated properties and stool amounts to a device to be displayed.

6 Claims, 10 Drawing Sheets

| RESULT ID | TARGET IMAGE | DETERMINATION INFORMATION | | | ... | ... |
|---|---|---|---|---|---|---|
| | | #1 | #2 | #3 | | |
| ... | ... | ... | ... | ... | ... | ... |
| RS11 | IM11 | Type1: SMALL | Type3: SMALL | Type4: LARGE | ... | ... |
| ... | ... | ... | ... | ... | ... | ... |

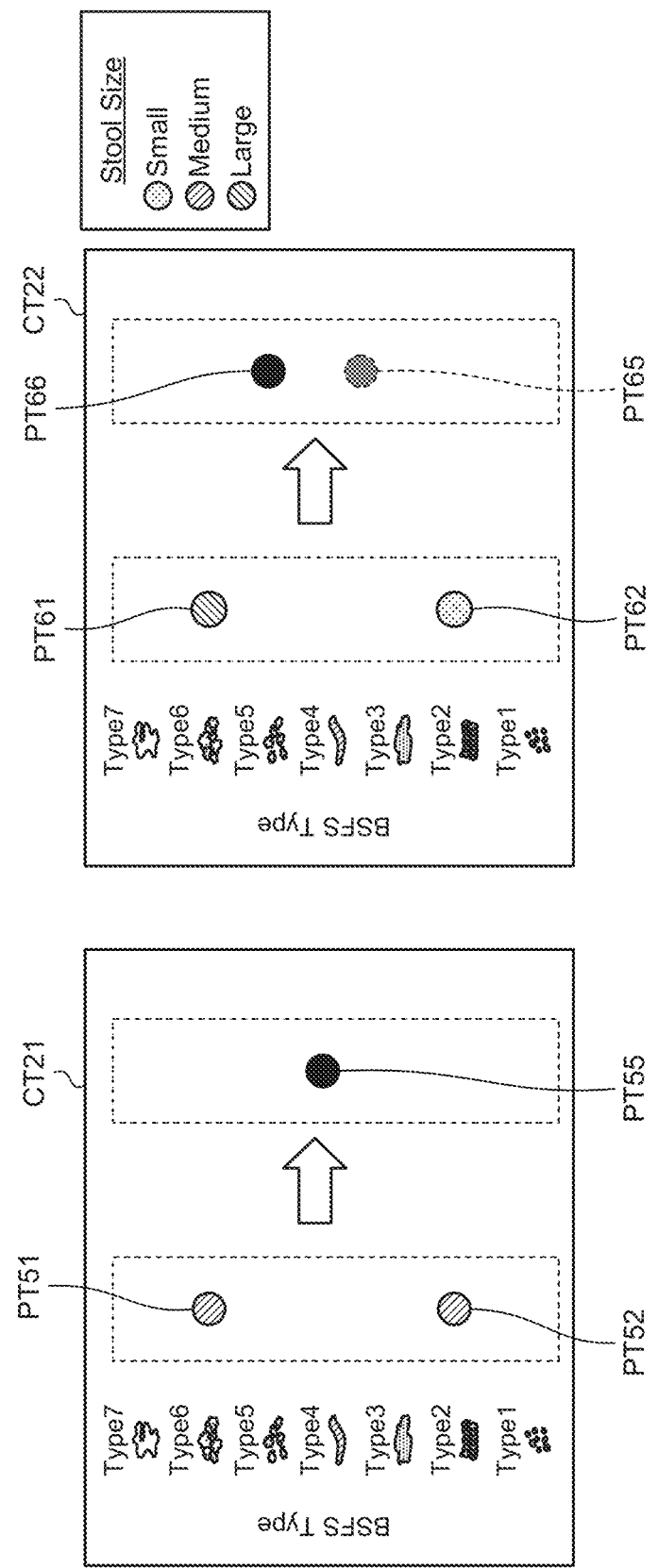

EXCREMENT JUDGEMENT SYSTEM, EXCREMENT JUDGEMENT METHOD, AND EXCREMENT JUDGEMENT DEVICE

FIELD

Embodiments of the disclosure relate to an excrement judgement system, an excrement judgement method, and an excrement judgement device.

BACKGROUND

Conventionally, there has been known a health management system that is based on a defecation record obtained by determining a property of a stool (also referred to as "excrement") from an image of excrement. For example, as a health management system, there has been disclosed a determination system that is capable of specifying representative stool from stool having a plurality of properties with respect to excrement in which various properties are mixed (see Patent Literature 1, for example). Additionally, for example, there has been disclosed a technology that estimates a property of excrement from a plurality of still images obtained by capturing a falling excrement (see Patent Literature 2, for example).

CITATION LIST

Patent Literature

Patent Literature 1: Japanese Laid-Open Patent Publication No. 2021-050983
Patent Literature 2: Japanese Patent No. 6742663

SUMMARY

Technical Problem

In such a conventional stool judgement system, for example, for a target person such as a user, which is a target of health management in a facility for the elderly and the like, care with respect to chronic constipation becomes late, and information is not sufficient for detecting a sign of constipation in early stages before it becomes serious and for precisely determining a constipation state of the target person. Specifically, for example, in a conventional stool judgement system, in case where determining a constipation state of a target person on the basis of information on a representative stool, there presents possibility that diagnostic of constipation and diagnostic of other symptoms are missed in case where a constipation stool is included in addition to the representative stool. For example, when a normal stool is continuously indicated as a representative stool even in a case where a constipation stool is included, there presents possibility that a manager who manages health condition of elderly persons erroneously recognizes a constipation state of an elderly person.

In a case where estimating change in a property of stool, a conventional stool judgement system is capable of detecting a defecation tendency that there presents possibility of constipation when a property changes from a loose stool to a hard stool. However, in the conventional stool judgement system, there presents possibility that information is not sufficient in case where a stool amount slightly changes without change in property, or a proportion of hard stool with respect to all stools increases in a daily defecation record, for example. Therefore, in the conventional stool judgement system, when dose administration is made, a subtle change of whether a chronic constipation state after the dose administration has a recovering tendency or a deteriorating tendency and whether or not a dosage is appropriate is unknown, and thus there presents possibility that erroneous care is provided to a target person. Thus, there has been desired to execute appropriate information output on stool so that health management of a target person is possible, such as care for an appropriate chronic constipation state.

In consideration of aforementioned, a problem is to execute appropriate information output on a stool.

It is an object of one aspect of embodiments to provide an excrement judgement system, an excrement judgement method, and an excrement judgement device capable of executing appropriate information output on a stool.

Solution to Problem

An excrement judgement system according to one aspect of embodiments including: an acquisition unit that acquires image information on an image in which excrement excreted in a defecation action per time is captured; a determination unit that determines properties of a plurality of stools included in the image information and stool amounts corresponding to the properties of the plurality of stools; and an outputting unit that associates the properties of the plurality of stools and the stool amounts corresponding to the properties of the plurality of stools that are determined by the determination unit, and outputs the associated properties and stool amounts to a device to be displayed.

In accordance with the excrement judgement system according to one aspect of the embodiments, for example, even in a case where a defecation action per time includes a plurality of stools (hereinafter, may be simply referred to as "stool") having different properties such as hard stool and loose stool, stool amounts corresponding to the properties of the stools are determined to be able to know in detail change in defecation condition of a target person, so that it is possible to use properties of not only a representative stool but also a plurality of different stools in grasping daily health condition. Thus, according to the excrement judgement system, for example, it is possible to acquire information on a state where normal stool is continuously displayed as representative stool even though constipation stool is included, a state where a property is not changed but a stool amount is slightly changed and a proportion of hard stool with respect to all stools is increased in a daily defecation record. Thus, according to the excrement judgement system, for example, in a case where a doctor administers a dose, it is possible to precisely know a subtle change of whether a chronic constipation state after the dose administration is in a recovering tendency or a deteriorating tendency, and whether or not the dosage is appropriate. Therefore, the excrement judgement system capable of executing appropriate information output with respect to stool. Thus, according to the excrement judgement system, it is possible to achieve early detection of a constipation tendency and more appropriate care for a chronic constipation state. Note that a defecation action per time corresponds to a defecation action from a time when a user (target person) of a toilet seats him/herself until the user unseats him/herself. In other words, the above-mentioned defecation action per time is in a concept including a case where there presets a plurality of defecations with intervals.

In the excrement judgement system according to one aspect of the embodiments, the outputting unit outputs, in a case where there presents a plurality of stools having a same property among stools whose properties are determined, a total value of stool amounts of the stools having the same property.

In accordance with the excrement judgement system according to one aspect of the embodiments, even in a case where a plurality of stools having the same property is separately discharged in a defecation action per time, a total amount obtained by totalizing the stools having the same property is displayed, so that it is possible to collect necessary information without scattering pieces of information related to the stools having the same property on a screen of an output destination. Therefore, the excrement judgement system capable of executing appropriate information output with respect to the stools. Thus, according to the excrement judgement system, it is possible to provide an easy-to-use service while providing detailed information to a manager that checks a defecation record, such as a health-care worker.

In the excrement judgement system according to one aspect of the embodiments, the outputting unit outputs, based on the properties of the plurality of stools in the defecation action per time, a representative value of the properties of the stools.

In accordance with the excrement judgement system according to one aspect of the embodiments, in a case where stools having different properties are discharged in a defecation action per time, it is possible not only to display types of respective stool properties thereof, but also to display a representative value in the defecation action per time. Therefore, the excrement judgement system is capable of execute appropriate information output with respect to stool. Thus, according to the excrement judgement system, a trend related to defecation condition of a user is able to be checked at a glance in recording daily health, so that it is possible to provide an easy-to-use service.

In the excrement judgement system according to one aspect of the embodiments, the outputting unit outputs, based on a ratio of a stool amount corresponding to the property of each of the stools to a total amount of stool amounts in the defecation action per time, a representative value of the properties of the stools.

In accordance with the excrement judgement system according to one aspect of the embodiments, a representative value is calculated on the basis of a ratio of each property with respect to a total amount of stool amounts in additionally displaying a representative value in a defecation action per time, so that it is possible to report a more precise tendency in defecation trend. Therefore, the excrement judgement system is capable of execute appropriate information output with respect to stool.

According to the excrement judgement system, in a case where a time-series defecation record in use of toilet at a plurality of times is checked, if a total stool amount is in a decreasing tendency, it is possible to find out in an early stage that a target person is in a hidden constipation state even when a dominant stool property in a defecation action per time is normal (normal stool), for example. Furthermore, according to the excrement judgement system, it is possible to determine a constipation tendency when a stool amount of simultaneously-discharged hard stool is in an increasing tendency even if a dominant stool property in a defecation action per time is normal (normal stool). In other words, according to the excrement judgement system, it is possible to determine a recovering tendency when a stool amount of simultaneously-discharged normal stool is in an increasing tendency even if a dominant stool property in a defecation action per time is abnormal (watery stool).

An excrement judgement method according to one aspect of the embodiments including: acquiring image information on an image in which excrement excreted in a defecation action per time is captured; determining properties of a plurality of stools included in the image information and stool amounts corresponding to the properties of the plurality of stools; associating the properties of the plurality of stools and the stool amounts corresponding to the properties of the plurality of stools that are determined in the determining; and outputting the associated properties and stool amounts to a device to be displayed.

In accordance with the excrement judgement method according to one aspect of the embodiments, for example, even in a case where a defecation action per time includes a plurality of stools having different properties such as hard stool and loose stool, stool amounts corresponding to the properties of the stools are determined to be able to know in detail change in defecation condition of a target person, so that it is possible to use properties of not only a representative stool but also a plurality of different stools in grasping daily health condition. Thus, according to the excrement judgement method, for example, it is possible to acquire information on a state where normal stool is continuously displayed as representative stool even though constipation stool is included, a state where a property is not changed but a stool amount is slightly changed and a proportion of hard stool with respect to all stools is increased in a daily defecation record. Thus, according to the excrement judgement method, for example, in a case where a doctor administers a dose, it is possible to precisely know a subtle change of whether a chronic constipation state after the dose administration is in a recovering tendency or a deteriorating tendency, and whether or not the dosage is appropriate. Therefore, the excrement judgement system capable of executing appropriate information output with respect to stool. Thus, according to the excrement judgement method, it is possible to achieve early detection of a constipation tendency and more appropriate care for a chronic constipation state.

An excrement judgement device according to one aspect of the embodiments including: an acquisition unit that acquires image information on an image in which excrement excreted in a defecation action per time is captured; a determination unit that determines properties of a plurality of stools included in the image information and stool amounts corresponding to the properties of the plurality of stools; and an outputting unit that associates the properties of the plurality of stools and the stool amounts corresponding to the properties of the plurality of stools that are determined by the determination unit, and outputs the associated properties and stool amounts to a device to be displayed.

In accordance with the excrement judgement device according to one aspect of the embodiments, for example, even in a case where a defecation action per time includes a plurality of stools having different properties such as hard stool and loose stool, stool amounts corresponding to the properties of the stools are determined to be able to know in detail change in defecation condition of a target person, so that it is possible to use properties of not only a representative stool but also a plurality of different stools in grasping daily health condition. Thus, according to the excrement judgement device, for example, it is possible to acquire information on a state where normal stool is continuously displayed as representative stool even though constipation stool is included, a state where a property is not changed but a stool amount is slightly changed and a proportion of hard stool with respect to all stools is increased in a daily defecation record. Thus, according to the excrement judgement device, for example, in a case where a doctor administers a dose, it is possible to precisely know a subtle change of whether a chronic constipation state after the dose administration is in a recovering tendency or a deteriorating tendency, and whether or not the dosage is appropriate. Therefore, the excrement judgement system capable of executing appropriate information output with respect to stool. Thus, according to the excrement judgement device, it is possible to achieve early detection of a constipation tendency and more appropriate care for a chronic constipation state.

Advantageous Effects of Invention

According to one aspect of embodiments, it is possible to execute appropriate information output on a stool.

BRIEF DESCRIPTION OF DRAWINGS

FIG. 13 is a diagram illustrating one example of displaying based on a representative value.

DESCRIPTION OF EMBODIMENTS

Hereinafter, embodiments of an excrement judgement system according to the present application will be described in detail with reference to the accompanying drawings. The present disclosure is not limited to the embodiments described in the following.

<1. Excrement Judgement Process>

Figure 1:
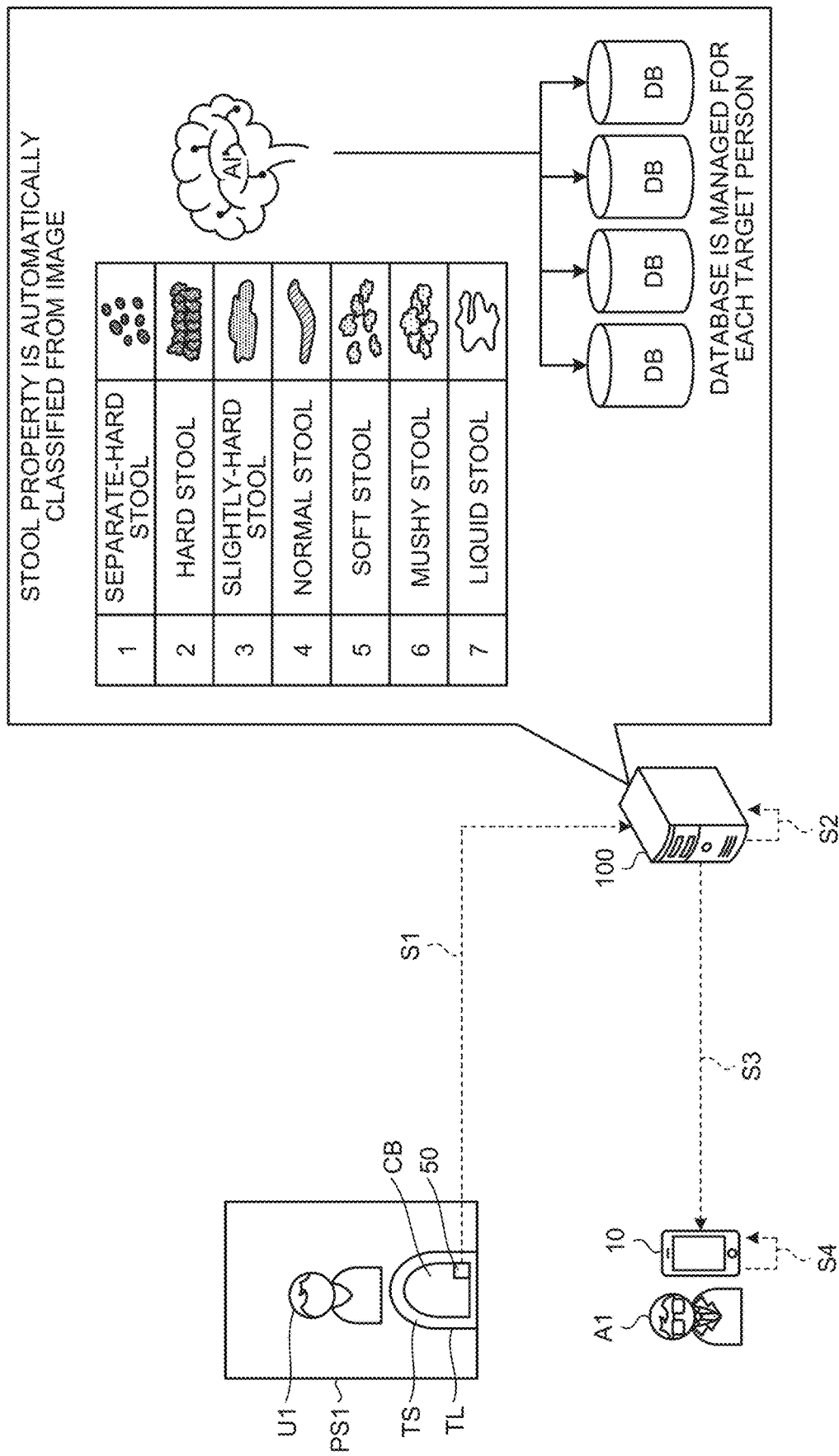
FIG. 1 is a diagram illustrating one example of an excrement judgement process according to an embodiment.

The outline of information processing to be executed in an excrement judgement system 1 (see FIG. 3) according to an embodiment will be explained with reference to FIG. 1. FIG. 1 is a diagram illustrating one example of the excrement judgement process according to the embodiment.

In an example illustrated in FIG. 1, a toilet space PS1 indicates a schematic plan view illustrating a toilet space in which a toilet device (hereinafter, may be referred to as "toilet TL") is arranged while exemplifying the toilet space PS1 provided in a facility for the elderly as one example of a toilet space. The example illustrated in FIG. 1 indicates a case where a sensor device 50 is arranged in a toilet seat TS of the toilet TL, which functions as an image sensor for detecting (capturing) an image of a water sealing part in a closet bowl CB of the toilet TL.

In FIG. 1, explanation is given while exemplifying a user U1 that is a target person (hereinafter, may be referred to as "user") to be a target of health management in a facility for the elderly as one example of a user of the toilet space PS1, and exemplifying a display device 10 used by a manager A1 that executes health management on the user U1, which is a target person, as one example of a device capable of displaying information (may be simply referred to as "device"). Note that the device is not limited to the display device 10, and this point will be mentioned later.

In the example illustrated in FIG. 1, the user U1 performs an excretion action (defecation action) in the toilet space PS1 in which the sensor device 50 is arranged, and the sensor device 50 captures a stool excreted by the user U1. The sensor device 50 captures an image that includes a plurality of stools excreted by the user U1 in a defecation action per time from when the user U1 seats him/herself on the toilet seat TS of the toilet TL to when unseats him/herself therefrom. As described above, a defecation action per time corresponds to a defecation action from when a user (target person) of a toilet seats him/herself to when unseats him/herself. For example, the toilet space PS1 is provided with a seating status detecting device that detects seating of a user on the toilet TL. For example, as the seating status detecting device, it is preferable that a human detecting sensor using infrared ray and the like is employed for avoiding erroneous detection of unseating when a user gets up a little. A human detecting sensor is merely one example, and the seating status detecting device is not limited to a human detecting sensor as long as seating of a user is able to be detected; and thus any device may be employed, such as a switch whose turning ON/OFF is switched by a load of a user who seats him/herself on the toilet seat TS.

Figure 2:
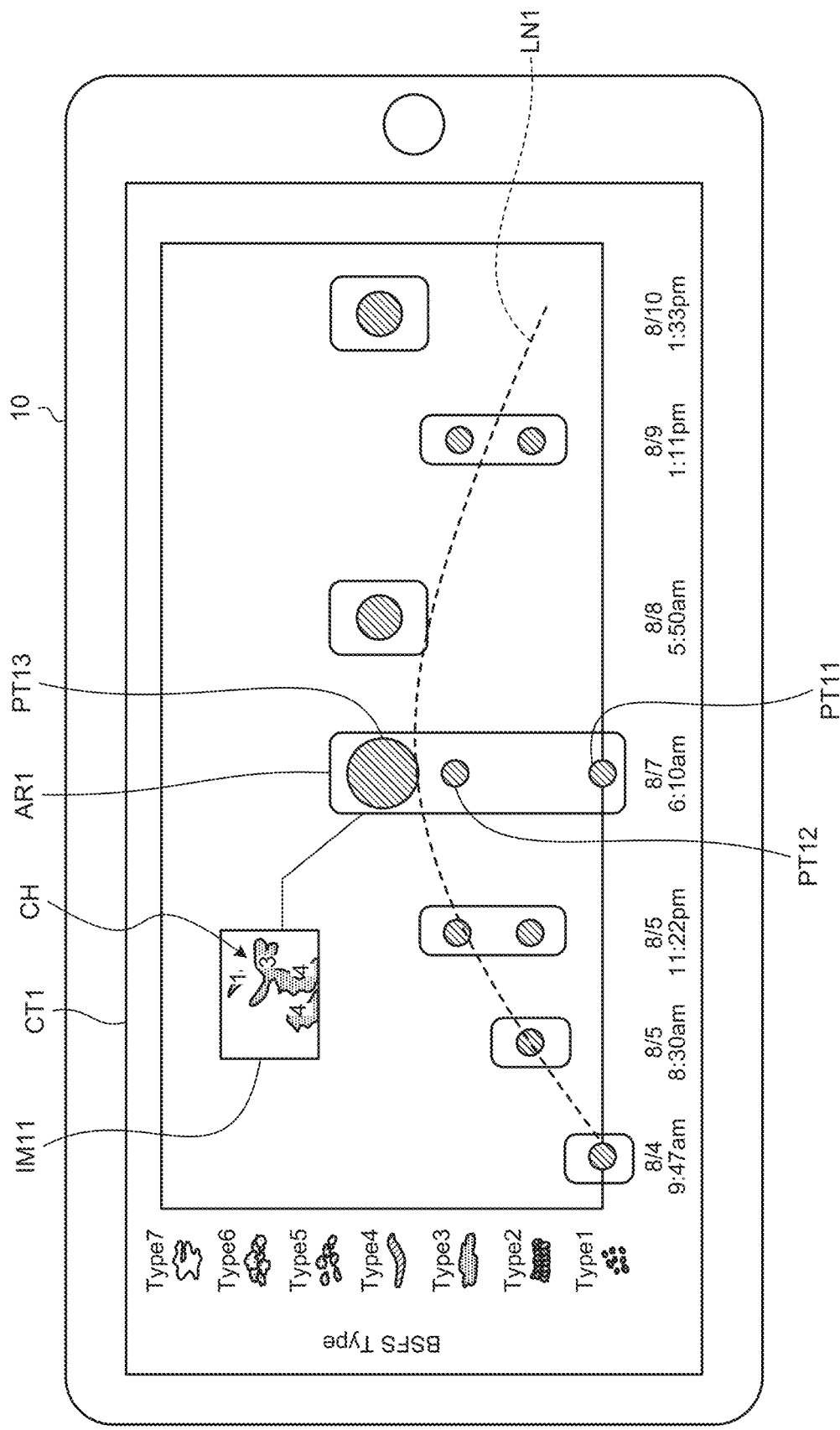
FIG. 2 is a diagram illustrating a displaying example of information related to excrement judgement.

For example, the sensor device 50 captures an image that includes a plurality of stools as indicated in an image IM11 illustrated in FIG. 2. In a case of the image IM11 indicated in FIG. 2, the sensor device 50 captures stools excreted by the user U1 at 6:10 on August 7th. The sensor device 50 captures a water sealing part of the closet bowl CB at 6:10 on August 7th so as to generate the image IM11 including a plurality of stools excreted by the user U1.

The sensor device 50 transmits an image obtained by capturing the stools excreted by the user U1 to an excrement judgement device 100 (Step S1). Thus, the excrement judgement device 100 acquires the image obtained by capturing stools excreted by the user U1. For example, the sensor device 50 transmits the captured image to the excrement judgement device 100 by using a secure communication method. For example, the sensor device 50 transmits an image encrypted by an encryption process to the excrement judgement device 100.

For example, the sensor device 50 transmits, to the excrement judgement device 100, date-and-hour information indicating a date and hour when the image is captured and target person information indicating that a target person of the image is the user U1, along with the image obtained by capturing stools excreted by the user U1. For example, the sensor device 50 transmits the image IM11 illustrated in FIG. 2 to the excrement judgement device 100, and the excrement judgement device 100 acquires the image IM11 illustrated in FIG. 2. For example, the excrement judgement device 100 transmits, to the excrement judgement device 100, date-and-hour information indicating that a date and hour at which the image IM11 is captured is 6:10 on August 7th and target person information (user ID, etc.) indicating that a target person of the image IM11 is the user U1, along with the image IM11. Note that the excrement judgement system 1 may execute specifying (personal authentication) that a person who uses the toilet space PS1 is the user U1, and this point will be mentioned later.

The excrement judgement device 100 executes a determination process for determining properties of a plurality of stools and stool amounts corresponding to the properties of the plurality of stools (Step S2). For example, the excrement judgement device 100 identifies a stool included in the image obtained by capturing excrement that is excreted by a defecation action per time. The excrement judgement device 100 determines properties of a plurality of stools and stool amounts corresponding to the properties of the plurality of stools while targeting the identified stool. The excrement judgement device 100 automatically classifies a stool property and an amount from the image. The excrement judgement device 100 manages a database for each target person. For example, the excrement judgement device 100 manages data in association with information (ID) that identifies a target person.

For example, the excrement judgement device 100 executes a process (may be also referred to as "stool identification determination process") for determining properties of a plurality of stools included in an image and stool amounts corresponding to the properties of the plurality of stools by using a technology related to machine learning such as artificial intelligence (AI). For example, the excrement judgement device 100 may determine respective properties of a plurality of stools and stool amounts corresponding to the properties of the plurality of stools while targeting the plurality of stools included in an image. In a case where, the excrement judgement device 100 identifies a plurality of stools included in an image, and determines respective properties of the plurality of stools and stool amounts corresponding to the properties of the plurality of stools. For example, the excrement judgement device 100 may target a single stool included in an image, and further may determine respective properties of the plurality of stools and stool amounts corresponding to the properties of the plurality of stools with respect to the single stool. In this case, the excrement judgement device 100 identifies a single lump (stool) included in an image, for example, and determines respective properties of a plurality of regions (stools) in the single lump and stool amounts corresponding to the properties of the plurality of regions. As described above, properties of a plurality of stools, which are determined in the stool identification determination process by the excrement judgement device 100, may be properties of respective stools that are divided into plural parts, or may be a plurality of properties included in a single stool. For example, a plurality of properties included in a single stool may be properties of a plurality of regions (parts) in a single lump (stool). As described above, a plurality of properties of stools may include a case where a plurality of properties is included in a single stool. The excrement judgement device 100 executes the stool identification determination process by using a machine learning model (hereinafter, may be referred to as "model") learned by machine learning. For example, the excrement judgement device 100 executes the stool identification determination process by using models M1 to M3 and the like learned by machine learning, and examples of the models will be mentioned later.

For example, the excrement judgement device 100 identifies properties of a plurality of stools included in an image by using a model of machine learning such as artificial intelligence (AI). For example, the excrement judgement device 100 specifies regions of respective stools in an image by using the model M1. For example, the excrement judgement device 100 determines that each of properties of a plurality of stools included in an image corresponds to which of seven types of Type1 to Type7 (hereinafter, may be indicated by using only number of 1 to 7 while omitting "Type") based on the Bristol stool scale, by using a model of machine learning such as artificial intelligence (AI). For example, by using the model M2, the excrement judgement device 100 determines that each of properties of a plurality of stools included in an image corresponds to which of seven types (stages) of separate-hard stool, hard stool, slightly-hard stool, normal stool, soft stool, mushy stool, and liquid stool. For example, the excrement judgement device 100 determines that an amount (size) of each of a plurality of stools included in an image corresponds to which of the plurality of stages, by using a model of machine learning such as artificial intelligence (AI). For example, the excrement judgement device 100 determines, by using the model M3, that an amount of each of a plurality of stools included in an image corresponds to which of three types (stages) of small-amount (small), middle, and large-amount (large). Note that the above-mentioned process is merely one example, and the stool identification determination process may be executed by any method as long as the excrement judgement device 100 is able to identify properties of a plurality of stools included in an image, and further to determine the properties of the plurality of stools and stool amounts corresponding to the properties of the plurality of stools.

The excrement judgement device 100 outputs a determination result to the display device 10 (Step S3). The excrement judgement device 100 transmits, to the display device 10, information obtained by associating properties of a plurality of stools and stool amounts corresponding to the properties of the plurality of stools with each other. For example, as illustrated in FIG. 2, the excrement judgement device 100 transmits, to the display device 10, a content CT1 that indicates information obtained by associating properties of stools corresponding to each defecation action per time and respective stool amounts corresponding to the properties of the stools with each other with respect to the user U1.

The display device 10 that receives the information from the excrement judgement device 100 displays the received information (Step S4). The display device 10 displays a received determination result. As illustrated in FIG. 2, the display device 10 displays the content CT1 that indicates information obtained by associating properties of stools corresponding to each defecation action per time and respective stool amounts corresponding to the properties of the stools with each other with respect to the user U1.

As described above, the excrement judgement system 1 determines properties of a plurality of stools included in an image and stool amounts corresponding to the properties of the plurality of stools while targeting the image in which excrement excreted at a defecation action per time is captured. The excrement judgement system 1 associates the determined properties of the plurality of stools and stool amounts corresponding to the properties of the plurality of stools with each other, and further outputs it to a device to be displayed. Thus, the excrement judgement system 1 is capable of executing appropriate information output with respect to stools. For example, the excrement judgement system 1 is capable of realizing care for chronic constipation by using the above-mentioned process while targeting elderly persons.

<2. Displaying Example>

A displaying example of information will be explained with reference to FIG. 2. FIG. 2 is a diagram illustrating a displaying example of information related to excrement judgement. For example, the content CT1 illustrated in FIG. 2 is displayed in a screen of the display device 10 such as a terminal device of a manager (health-care worker, etc.) that recognizes a defecation record. Specifically, in FIG. 2, a case is illustrated where the display device 10, which is a device, displays in time series determination results corresponding to respective defecation actions per time of a target person. For example, the display device 10 displays in time series data indicating a determination result based on the Bristol stool scale and the like for each person (target person). Moreover, the display device 10 is capable of displaying an image of excreted stools. The display device 10 displays information that expresses defecation trend by using an approximation curve. The display device 10 displays information that expresses a size (large middle small) of a stool. This point will be explained below with reference to the content CT1 illustrated in FIG. 2. Note that explanation is proceeded with reference to FIG. 2 while exemplifying a case where the user U1 illustrated in FIG. 1 is a target person.

The excrement judgement device 100 generates the content CT1 that indicates in time series information obtained by associating properties of a plurality of stools and stool amounts corresponding to the properties of the plurality of stools with each other with respect to the user U1. For example, the excrement judgement device 100 generates the content CT1 including a graph that expresses an amount (size) of a stool by using a size of a plotted point (circle), and a lateral axis (X-axis) corresponds to time series and a vertical axis (Y-axis) corresponds to a property of stool. The content CT1 indicates that a property corresponds to one of the seven stages from Type1 to Type7 by using a position in a direction of the vertical axis (Y-axis), and further indicates that a value of the property (Type) is higher as a position in the direction of the vertical axis (Y-axis) is higher. For example, the content CT1 indicates an expression mode in which a position overlapped with a lower end along the lateral axis corresponds to a position corresponding to a property of Type1, and a position overlapped with an upper end along the lateral axis is a position corresponding to a property of Type7. In FIG. 2, the excrement judgement device 100 generates the content CT1 indicating that, with respect to the user U1, a defecation action per time corresponding to 6:10 on August 7th includes a stool whose stool property is Type1, a stool whose stool property is Type3, and a stool whose stool property is Type4.

For example, the excrement judgement device 100 determines, by using the image IM11, that a defecation action per time of the user U1 corresponding to 6:10 on August 7th includes a stool whose stool property is Type1, a stool whose stool property is Type3, and a stool whose stool property is Type4. The excrement judgement device 100 determines, by using the image IM11, that an amount of Type1-stool at 6:10 on August 7th is small. The excrement judgement device 100 determines, by using the image IM11, that an amount of Type3-stool at 6:10 on August 7th is small. The excrement judgement device 100 determines, by using the image IM11, that an amount of Type4-stool at 6:10 on August 7th is large. For example, the image IM11 is an image that includes the largest amount of stool of images having been captured at the defecation action per time of the user U1 corresponding to 6:10 on August 7th.

The excrement judgement device 100 generates the content CT1 obtained by associating a plurality of properties of stools with stool amounts corresponding to the respective properties. The excrement judgement device 100 generates the content CT1 that includes a plurality of circles having shapes PT11 to PT13 corresponding to respective stool properties as indicated in a region AR1, with respect to a defecation action per time of the user U1 corresponding to 6:10 on August 7th. The excrement judgement device 100 generates the content CT1 in which the shape PT11 whose stool property corresponds to Type1-stool, the shape PT12 whose stool property corresponds to Type3-stool, and the shape PT13 whose stool property corresponds to Type4-stool are arranged in the region AR1.

In FIG. 2, the excrement judgement device 100 generates the content CT1 that expresses a stool amount corresponding to a property for each of a plurality of properties of stools by using a size of a circle. An amount of Type1-stool at 6:10 on August 7th is small, and thus the excrement judgement device 100 generates the content CT1 that expresses the shape PT11 corresponding to Type1-stool by using a size corresponding to a stool amount "small". An amount of Type3-stool at 6:10 on August 7th is small, and thus the excrement judgement device 100 generates the content CT1 that expresses the shape PT12 corresponding to Type3-stool by using a size corresponding to a stool amount "small". An amount of Type4-stool at 6:10 on August 7th is large, and thus the excrement judgement device 100 generates the content CT1 that expresses the shape PT13 corresponding to Type4-stool by using a size corresponding to a stool amount "large".

In FIG. 2, the excrement judgement device 100 generates the content CT1 that expresses the shape PT13 corresponding to Type4-stool at 6:10 on August 7th by using a circle that is larger than the shape PT11 corresponding to Type1-stool and the shape PT12 corresponding to Type3-stool. As described above, the excrement judgement device 100 generates the content CT1 that expresses amounts of stools corresponding to a plurality of properties by using sizes of circles.

Similarly, with respect to another defecation action per time, the excrement judgement device 100 also determines properties and amounts of stool, and further generates the content CT1 that expresses determination result in a mode corresponding to the determined properties and amounts.

For example, with respect to a defecation action per time of the user U1 corresponding to 9:47 on August 4th, the excrement judgement device 100 determines that a property of stool is Type1, and further determines that an amount of Type1-stool is small. Thus, the excrement judgement device 100 generates the content CT1 that expresses excretion of Type1-stool at 9:47 on August 4th by using a circle whose size is corresponding to a stool amount "small".

For example, with respect to a defecation action per time of the user U1 corresponding to 11:22 on August 5th, the excrement judgement device 100 determines that properties of a plurality of stools are Type2 and Type3, and further determines that a stool amount of each of Type2 and Type3 is small. Thus, the excrement judgement device 100 generates the content CT1 that expresses excretion of Type2-stool and Type3-stool at 11:22 on August 5th by using two circles each having a size corresponding to a stool amount "small".

For example, with respect to a defecation action per time of the user U1 corresponding to 5:50 on August 8th, the excrement judgement device 100 determines that a property of stool is Type4, and further determines that an amount of Type4-stool is middle. Thus, the excrement judgement device 100 generates the content CT1 that expresses excretion of Type4-stool at 5:50 on August 8th by using a circle whose size is corresponding to a stool amount "middle".

Thus, the excrement judgement device 100 generates the content CT1 that expresses a property of stool by a position along a vertical axis, and further expresses an amount (size) of stool by using a size of a plotted point (circle). The excrement judgement device 100 generates information that indicates in time series information obtained by associating properties of a plurality of stools and stool amounts corresponding to the properties of the plurality of stools with each other.

Note that in FIG. 2, the excrement judgement device 100 generates the content CT1 that includes information other than the information that indicates in time series information obtained by associating properties of a plurality of stools and stool amounts corresponding to the properties of the plurality of stools with each other.

For example, the excrement judgement device 100 generates information indicating a tendency in defecation of a target person. In FIG. 2, the excrement judgement device 100 generates the content CT1 including a trend line LN1 that is information indicating a time-course tendency in defecation of the user U1 that is a target person. The trend line LN1 in the content CT1 is information that expresses defecation trend by using an approximation curve. The excrement judgement device 100 generates the trend line LN1 that expresses a time-course transition of data related to defecation of the user U1 by appropriately using various technologies related to derivation of an approximation curve.

Thus, the excrement judgement device 100 is capable of presenting, to a manager that checks the information and the like, an overall tendency in defecation of a target person so that the manager is able to grasp the tendency at a glance. In other words, the excrement judgement device 100 is capable of causing a manager that checks the information and the like to intuitively recognize an overall tendency in defecation of a target person. Therefore, the excrement judgement device 100 is capable of shortening a time interval needed for a manager that checks the information and the like to recognize defecation of a target person. The approximation curve is not limited to the trend line LN1 illustrated in FIG. 2, and may be various lines.

For example, the excrement judgement device 100 generates the content CT1 obtained by associating an image corresponding to each defecation action per time with a display position corresponding to a corresponding defecation action per time. In FIG. 2, the excrement judgement device 100 generates the content CT1 obtained by associating the image IM11 corresponding to a defecation action per time at 6:10 on August 7th with a part (for example, region AR1) corresponding to 6:10 on August 7th on the lateral axis. For example, the excrement judgement device 100 generates the content CT1 that displays the image IM11 when an operator of the display device 10 specifies a part (for example, region AR1) corresponding to 6:10 on August 7th on the lateral axis. In this case, the excrement judgement device 100 may generate the content CT1 that displays the image IM11 when an operator of the display device 10 clicks the region AR1.

In FIG. 2, the excrement judgement device 100 may generate the content CT1 that displays, on the image IM11 in a superposed manner, character information CH that indicates stool properties corresponding to respective stools in the image IM11. The character information CH is a number that indicates a property of stool (Type) in the image IM11. In FIG. 2, the excrement judgement device 100 may generate the content CT1 that displays, on the image IM11 in a superposed manner, "1" in a region of stool whose property is Type1, "3" in a region of stool whose property is Type3, and "4" in a region of stool whose property is Type4.

The excrement judgement device 100 outputs the content CT1 to the display device 10. For example, the excrement judgement device 100 transmits the content CT1 to the display device 10. The display device 10 displays the received content CT1. Thus, the display device 10 displays a plurality of stool amounts corresponding to properties of a plurality of stools included in a defecation action per time. The content CT1 illustrated in FIG. 2 indicates a state where the image IM11 is displayed; however, it is possible that an image IM is not displayed until an operator of the display device 10 specifies the displaying.

The display device 10 displays the content CT1 that displays in time series information obtained by associating properties of a plurality of stools and stool amounts corresponding to the properties of the plurality of stools with each other, with respect to the user U1. For example, the display device 10 displays the content CT1 including a graph that expresses an amount (size) of a stool by using a size of a plotted point (circle), and a lateral axis (X-axis) corresponds to time series and a vertical axis (Y-axis) corresponds to a property of stool. The display device 10 displays the content CT1 indicating that a defecation action per time corresponding to 6:10 on August 7th with respect to the user U1 includes a stool whose stool property is Type1, a stool whose stool property is Type3, and a stool whose stool property is Type4.

In FIG. 2, the display device 10 displays the content CT1 including the trend line LN1 that is information indicating a time-course tendency in defecation of the user U1 that is a target person. The display device 10 displays the image IM11 when an operator of the display device 10 specifies a part (for example, region AR1) corresponding to 6:10 on August 7th on the lateral axis. In this case, the display device 10 displays the image IM11 when an operator of the display device 10 clicks the region AR1.

Note that in FIG. 2, when displaying the image IM11, the display device 10 displays, on the image IM11 in a superposed manner, the character information CH indicating stool properties corresponding to respective stools in the image IM11. In FIG. 2, when displaying the image IM11, the display device 10 displays, on the image IM11 in a superposed manner, "1" for a region of stool whose property is Type1, "3" for a region of stool whose property is Type3, and "4" for a region of stool whose property is Type4.

<3. Configuration of Excrement Judgement System>

Figure 3:
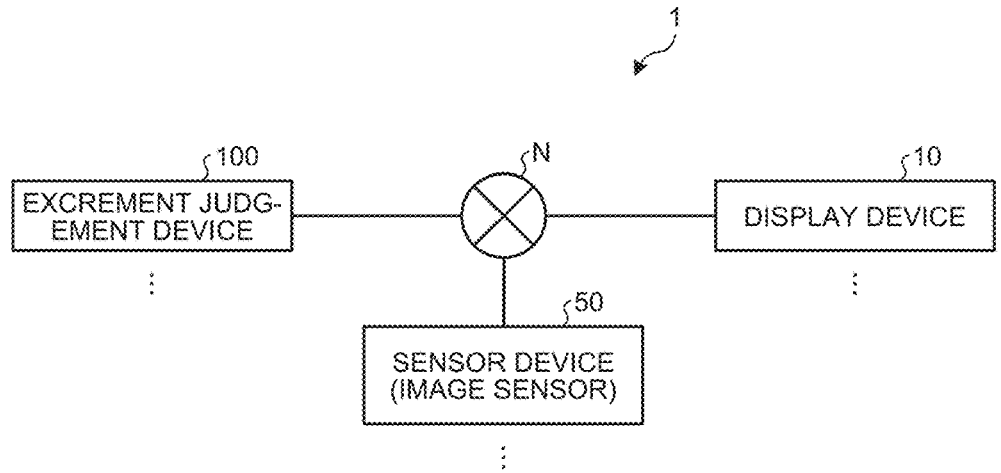
FIG. 3 is a diagram illustrating a configuration example of an excrement judgement system according to the embodiment.

Next, a configuration of the excrement judgement system 1 will be explained with reference to FIG. 3. FIG. 3 is a diagram illustrating a configuration example of the excrement judgement system according to the embodiment. Specifically, a configuration of the excrement judgement system 1 is illustrated in FIG. 3. The excrement judgement system 1 includes the excrement judgement device 100, the sensor device 50, and the display device 10. The excrement judgement system 1 may include the plurality of excrement judgement devices 100, the plurality of sensor devices 50, and the plurality of display devices 10.

The excrement judgement device 100 is an information processing device (computer) configured to determine properties of a plurality of stools included in an image obtained by capturing excrement that is excreted by a defecation action per time and stool amounts corresponding to the properties of the plurality of stools. The excrement judgement device 100 associates the determined properties of a plurality of stools and the determined stool amounts corresponding to the properties of the plurality of stools with each other, and further outputs it to a device to be displayed. The excrement judgement device 100 includes a database such as a storage 120 (see FIG. 4) so as to execute an excrement judgement process. For example, the excrement judgement device 100 may be installed in the toilet TL, or may be a server device (cloud server) used in the cloud or the like.

The excrement judgement device 100 is connected to the sensor device 50 and the display device 10 via a predetermined network N such as the Internet to be able to communicate with each other in a wired or wireless manner. The excrement judgement device 100 may be connected to the sensor device 50 and the display device 10 in a wired manner to be able to communicate with each other, or may be connected in a wireless manner to be able to communicate with each other as long as information is able to be transmitted and received.

The sensor device 50 is an image sensor that detects (captures) an image of a water sealing part in the closet bowl CB of the toilet TL. The sensor device 50 has communication function that is realized by a communication circuit and the like, and transmits information related to an image of a water sealing part in the closet bowl CB of the toilet TL to the excrement judgement device 100. The sensor device 50 is arranged in the toilet space PS1 so as to capture (detect) stool of a target person excreted into the closet bowl CB of the toilet TL. For example, the sensor device 50 is arranged in a toilet seat or a closet bowl in a toilet space. Note that the sensor device 50 may be arranged in, not limited to a toilet seat or a closet bowl, any part as long as being arranged in a position capable of detecting stool of a target person excreted into the closet bowl CB of the toilet TL.

The example illustrated in FIG. 1 indicates a case where the sensor device 50 is arranged in the toilet seat TS of the toilet TL; however, the sensor device 50 may be arranged in any part in the toilet space PS1 as long as being capable of detecting an image of a water sealing part in the closet bowl CB of the toilet TL. For example, the sensor device 50 may be arranged in a part other than the toilet TL such as the closet bowl CB of the toilet TL. The sensor device 50 may be provided such that a part (sensor) for detecting (capturing) an image of a water sealing part in the closet bowl CB of the toilet TL is separately arranged from a part (communication circuit, etc.) having communication function.

The sensor device 50 includes an image sensor (image sensor) that captures stool excreted into the closet bowl CB of the toilet TL. The sensor device 50 may include any type sensor as long as being capable of capturing stool excreted into the closet bowl CB of the toilet TL.

The display device 10 is an information processing device to be used by a manager that executes health management on a target person and the like. The display device 10 is realized by, for example, a smartphone, a mobile telephone, a Personal Digital Assistant (PDA), a tablet terminal, a laptop Personal Computer (PC), or the like. The example illustrated in FIG. 1 indicates a case where the display device 10 is a tablet terminal to be used by a manager that is a health-care worker executing health management on elderly persons that are target persons.

The display device 10 is a device that displays properties of a plurality of stools and stool amounts corresponding to the properties of the plurality of stools in association with each other. The display device 10 is connected to the excrement judgement device 100 to be able to communicate with each other via the Internet (predetermined network N, etc.) so as to transmit and receive information to and from the excrement judgement device 100. The display device 10 receives, from the excrement judgement device 100, a content indicating properties of a plurality of stools and stool amounts corresponding to the properties of the plurality of stools in association with each other, and displays the received content.

<4. Functional Configuration of Devices>

Hereinafter, functional configurations of the excrement judgement device 100 and the display device 10 that is one example of the device will be specifically explained.

<4-1. Functional Configuration of Excrement Judgement Device>

Figure 4:
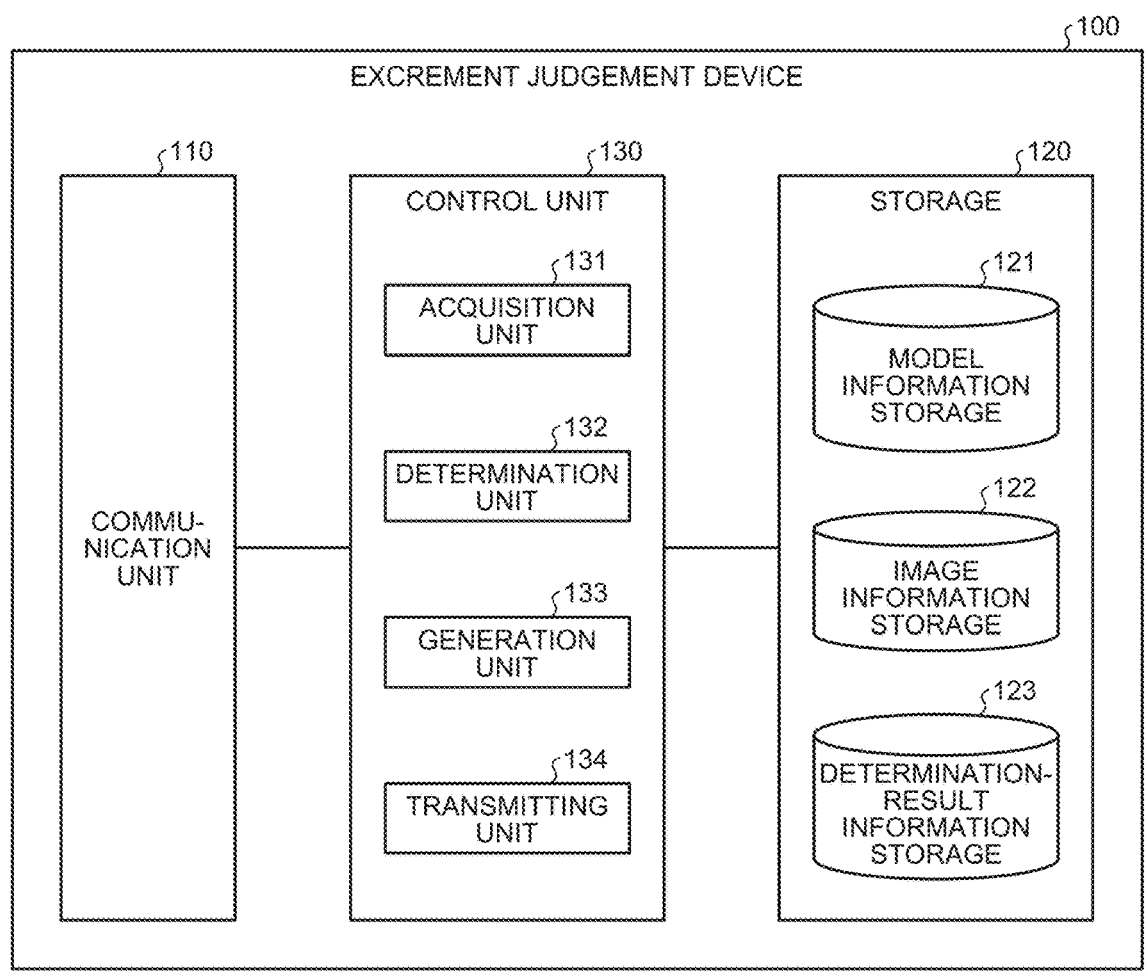
FIG. 4 is a block diagram illustrating one example of a configuration of an excrement judgement device according to the embodiment.

First, a functional configuration of the excrement judgement device will be explained with reference to FIG. 4. FIG. 4 is a block diagram illustrating one example of a configuration of the excrement judgement device according to the embodiment.

As illustrated in FIG. 4, the excrement judgement device 100 includes a communication unit 110, the storage 120, and a control unit 130. The excrement judgement device 100 may include an input unit (for example, keyboard, mouse, etc.) that receives various operations from a manager of the excrement judgement device 100 and the like and a display (for example, liquid crystal display, etc.) for displaying various kinds of information.

The communication unit 110 is realized by, for example, a communication circuit and the like. The communication unit 110 is connected to the predetermined network N (see FIG. 3) in a wired or wireless manner so as to transmit and receive information to and from an external information processing device. For example, the communication unit 110 is connected to the predetermined network N (see FIG. 3) in a wired or wireless manner so as to transmit and receive information to and from the display device 10, a toilet operating device, and the like.

The storage 120 is realized by a semiconductor memory element such as a Random Access Memory (RAM) and a flash memory, or a storage such as a hard disk and an optical disk. For example, the storage 120 is a computer-readable recording medium that non-transitorily records therein a determination program for determining properties of a plurality of stools included in image information and stool amounts corresponding to the properties of the plurality of stools, data used by the determination program, and the like. As illustrated in FIG. 4, the storage 120 according to the embodiment includes a model information storage 121, an image information storage 122, and a determination-result information storage 123.

Figure 5:
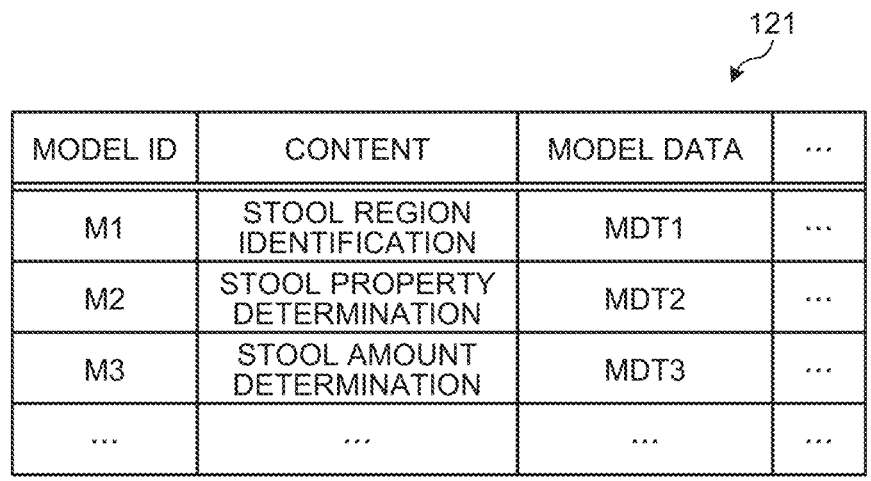
FIG. 5 is a diagram illustrating one example of a model information storage according to the embodiment.

The model information storage 121 according to the embodiment stores therein information related to models. For example, the model information storage 121 stores therein model information (model data) to be used in various processes. For example, the model information storage 121 stores therein information on models used for identifying a stool included in image information, a property determining program for determining properties of a plurality of stools, and a stool amount determining model for determining stool amounts corresponding to the properties of the plurality of stools. FIG. 5 is a diagram illustrating one example of the model information storage according to the embodiment. For example, the model information storage 121 stores therein information related to a facility. The model information storage 121 illustrated in FIG. 5 includes items such as "model ID", "content", and "model data".

The "model ID" indicates identification information for identifying a model. The "content" indicates usage (content) of a corresponding model. The "model data" indicates data of a model. In FIG. 5, the example is illustrated where conceptual information such as "MDT1" is stored in "model data"; actually, various kinds of information constituting the model is included, such as information related to a network included in the model and an arithmetic function.

FIG. 5 indicates that usage (content) of a model (model M1) identified by a model ID "M1" is "stool region identification". Model data of the model M1 indicates model data MDT1. For example, the model M1 detects a boundary of a stool included in an image, and further outputs information indicating the boundary. For example, the model M1 receives an input of an image captured by the sensor device 50, and further outputs information (region information) indicating a region (stool region) of stool included in the input image.

The model M1 is learned by using teacher data. For example, the model M1 is learned by using teacher data that is a combination of stool-region correct-answer information including a region of stool included in an image which is specified by an operator such as a doctor, and the image. A learning process for learning the model M1 may be executed by the excrement judgement device 100, or may be executed by a device (learning device) other than the excrement judgement device 100. In a case where a learning device learns the model M1, the excrement judgement device 100 receives the model M1 from the learning device. The model M1 may have any configuration as long as being capable of realizing desired processes, and an arbitrary configuration such as a neural network may be employed.

Usage (content) of a model (model M2) that is identified by a model ID "M2" is indicated to be "stool property determination". Model data of the model M2 indicates model data MDT2. For example, the model M2 outputs determination result of a stool property indicating classification of seven types based on the Bristol stool scale for each stool included in an input image. For example, the model M2 receives an input including region information indicating a region of stool and an image captured by the sensor device 50, and further outputs information (property information) indicating a property of stool (Type) included in the region indicated by the region information in the input image. For example, the model M2 outputs information indicating that a property of stool (Type) included in the image corresponds to one of the seven stages 1 to 7.

The model M2 is learned by using teacher data. For example, the model M2 is learned by using teacher data that is a combination of stool-property correct-answer information including a property of stool included in an image which is specified by an operator such as a doctor, and the image. For example, the model M3 is learned by using teacher data that is a combination of stool-amount correct-answer information indicating that a property of stool included in an image corresponds to one of the seven levels of 1 to 7, and the image. A learning process for learning the model M2 may be executed by the excrement judgement device 100, or may be executed by a device (learning device) other than the excrement judgement device 100. In a case where a learning device learns the model M2, the excrement judgement device 100 receives the model M2 from the learning device. The model M2 may have any configuration as long as being capable of realizing desired processes, and an arbitrary configuration such as a neural network may be employed.

Usage (content) of a model (model M3) that is identified by a model ID "M3" is indicated to be "stool amount determination". Model data of the model M3 indicates model data MDT3. For example, the model M3 outputs determination result of a stool amount (size) indicating classification of the plurality of stages for each stool included in an input image. For example, the model M3 receives an input including region information indicating a region of stool and an image captured by the sensor device 50, and further outputs information(amount information) indicating an amount (size) of stool included in a region indicated by the region information in the input image. For example, the model M3 outputs information indicating that an amount (size) of stool included in an image is one of three stages of small (for example, "1"), middle (for example, "2"), and large (for example, "3").

The model M3 is learned by using teacher data. For example, the model M3 is learned by using teacher data that is a combination of stool-amount correct-answer information including an amount (size) of stool included in an image which is specified by an operator such as a doctor, and the image. For example, the model M3 is learned by using teacher data that is a combination of stool-amount correct-answer information indicating that an amount of stool included in an image is one of three levels of small, middle, and large; and the image. A learning process for learning the model M3 may be executed by the excrement judgement device 100, or may be executed by a device (learning device) other than the excrement judgement device 100. In a case where a learning device learns the model M3, the excrement judgement device 100 receives the model M3 from the learning device. The model M3 may have any configuration as long as being capable of realizing desired processes, and an arbitrary configuration such as a neural network may be employed.

The model information storage 121 may store therein, not limited to the aforementioned, various kinds of information depending on the purpose. For example, the model information storage 121 stores therein parameter information on a model learned (generated) in a learning process. Learning methods of the models M1 to M3 and the like are not limited to the above-mentioned methods, and an arbitrary well-known technology may be employed. The models may be learned by appropriately using various conventional technologies related to machine learning. For example, the models may be learned by using a technology related to machine learning of supervised learning such as a Support Vector Machine (SVM). For example, the models may be learned by using a technology of deep learning. For example, the models may be learned by appropriately using various technologies of deep learning, such as a Deep Neural Network (DNN), a Recurrent Neural Network (RNN), and a Convolutional Neural Network (CNN). The above description related to learning of models is merely one example, and the models may be learned by a learning method that is appropriately selected in accordance with acquirable information and the like.

Figure 6:
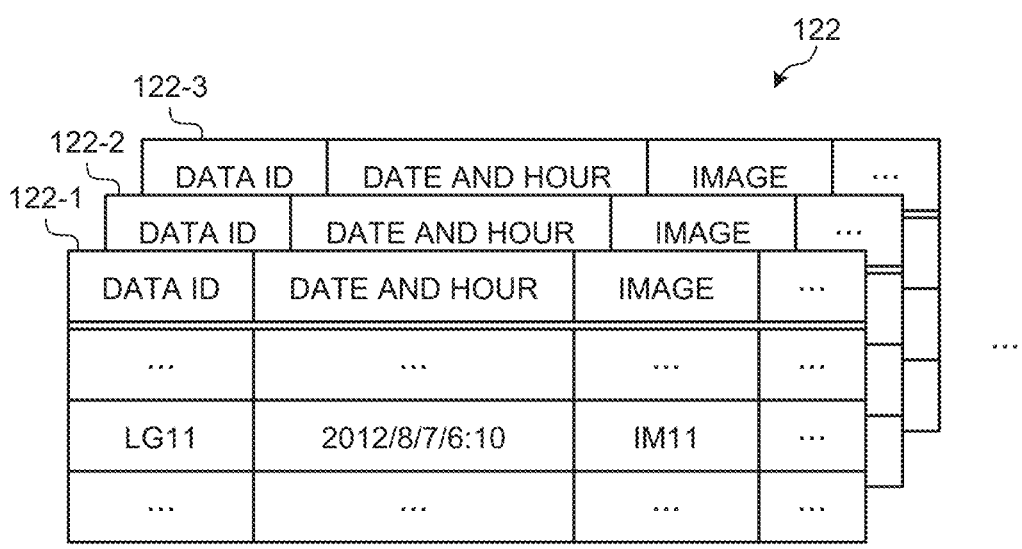
FIG. 6 is a diagram illustrating one example of an image information storage according to the embodiment.

The image information storage 122 according to the embodiment stores therein information related to images. For example, the image information storage 122 stores therein images obtained by capturing excrement (stool). FIG. 6 is a diagram illustrating one example of the image information storage according to the embodiment. In the example illustrated in FIG. 6, the image information storage 122 individually stores pieces of information for each of users, for example, an image information storage 122-1, an image information storage 122-2, an image information storage 122-3, etc. For example, the image information storage 122-1, the image information storage 122-2, the image information storage 122-3, etc. may be stored in respective different databases.

For example, the image information storage 122-1 indicates information related to images with respect to a user (corresponding to "user U1" illustrated in FIG. 1) that is identified by a user ID "U1". For example, the image information storage 122-2 indicates information related to images with respect to a user that is identified by a user ID "U2". For example, the image information storage 122-3 indicates information related to images with respect to a user that is identified by a user ID "U3".

Each of the image information storage 122-1, the image information storage 122-2, the image information storage 122-3, etc. illustrated in FIG. 6 includes items such as "data ID", "date and hour", and "image". Note that each of the image information storage 122-1, the image information storage 122-2, the image information storage 122-3, etc. may include an item (user ID and the like) for storing information that identifies a user.

The "data ID" indicates identification information for identifying each piece of data (image). The "date and hour" indicates a date and hour when the data is acquired. For example, "date and hour" indicates a date and hour when the image is detected (captured). The "image" indicates data of an image. In FIG. 6, the example is illustrated where conceptual information such as "IM11" is stored in "image", actually, corresponding image data itself, a file path name indicating a stored position thereof, and the like are stored.

In FIG. 6, data (image IM11) identified by a data ID "LG11" in the image information storage 122-1 is indicated to be an image that is acquired at a date and hour of "6:10 on Aug. 7, 2012". For example, illustrated is that an image of excrement of the user U1 is stored in the image information storage 122-1, such as the image IM11 of excrement of the user U1 which is captured at 6:10 on Aug. 7, 2012.

Note that the image information storage 122 may store, not limited to the aforementioned, various kinds of information depending on the purpose.

Figures 7, 8:
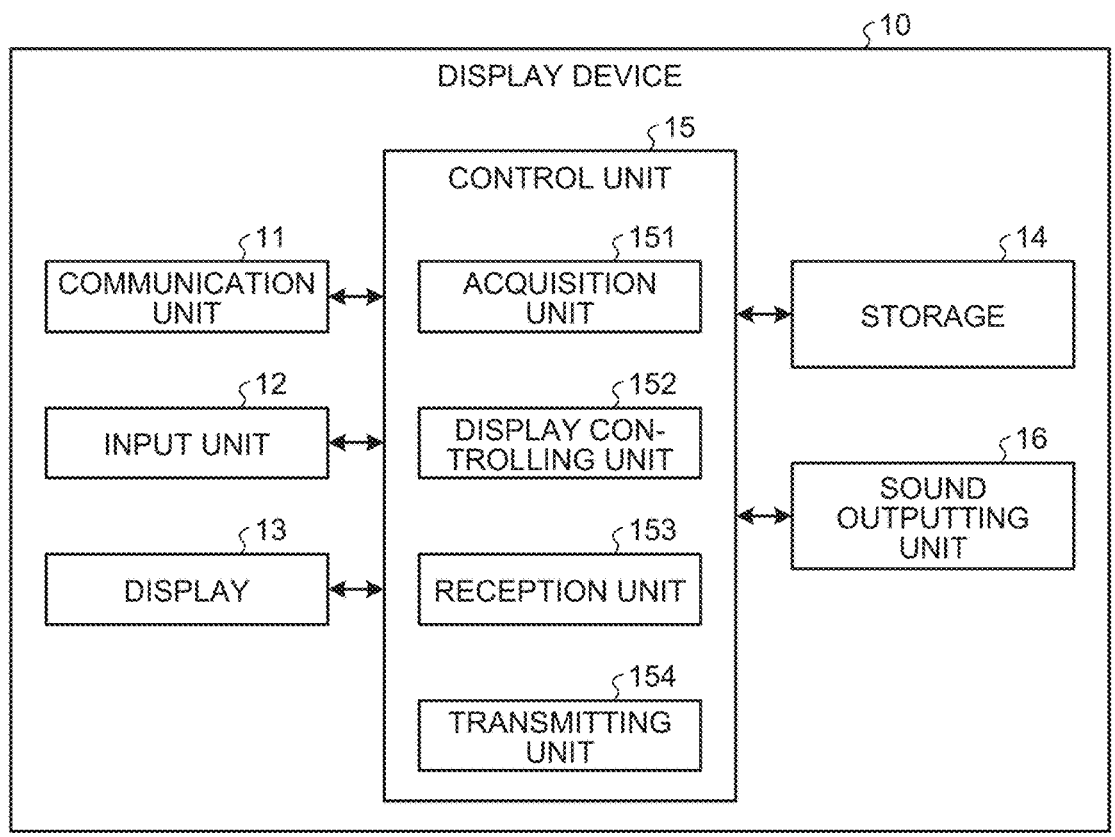
FIG. 7 is a diagram illustrating one example of a determination-result information storage according to the embodiment.
FIG. 8 is a block diagram illustrating one example of a configuration of a display device according to the embodiment.

The determination-result information storage 123 according to the embodiment stores therein various kinds of information related to determination result. For example, the determination-result information storage 123 stores therein various kinds of information related to determination result of excrement (stool). FIG. 7 is a diagram illustrating one example of the determination-result information storage according to the embodiment. In the example illustrated in FIG. 7, the determination-result information storage 123 individually stores pieces of information for each of users, for example, a determination-result information storage 123-1, a determination-result information storage 123-2, a determination-result information storage 123-3, etc. For example, the determination-result information storage 123-1, the determination-result information storage 123-2, the determination-result information storage 123-3, etc. may be stored in respective different databases.

For example, the determination-result information storage 123-1 indicates information related to images with respect to a user (corresponding to "user U1" illustrated in FIG. 1) that is identified by the user ID "U1". For example, the determination-result information storage 123-2 indicates information related to images with respect to a user that is identified by the user ID "U2". For example, the determination-result information storage 123-3 indicates information related to images with respect to a user that is identified by the user ID "U3".

Each of the determination-result information storage 123-1, the determination-result information storage 123-2, the determination-result information storage 123-3, etc. illustrated in FIG. 7 includes items such as "result ID", "target image", and "determination information". Note that each of the determination-result information storage 123-1, the determination-result information storage 123-2, the determination-result information storage 123-3, etc. may include an item (user ID and the like) for storing information that identifies a user.

The "result ID" indicates identification information for identifying determination result. The "target image" indicates an image that is a determination target. In FIG. 7, the example is illustrated where images are stored in "target image"; however, information (data ID) for identifying an image may be stored in "target image". The "determination information" indicates determination result such as a property and an amount of stool. In FIG. 7, the example illustrated in which "determination information" includes "#1", "#2", and "#3"; however, "determination information" includes items whose number corresponds to the number of determination results such as "#4", "#5", and "#6".

In the determination-result information storage 123-1 illustrated in FIG. 7, a determination result (result RS11) identified by a result ID "RS11" indicates a determination result with respect to the image IM11. The result RS11 indicates that determination information includes Type1-stool whose stool amount is small, Type3-stool whose stool amount is small, and Type4-stool whose stool amount is large. For example, illustrated is a determination result of an image of excrement of the user U1 is stored in the determination-result information storage 123-1, such as a determination result indicating that in the image IM11 of excrement of the user U1, determination information includes Type1-stool whose stool amount is small, Type3-stool whose stool amount is small, and Type4-stool whose stool amount is large.

Note that the determination-result information storage 123 may store, not limited to the aforementioned, various kinds of information depending on the purpose. For example, in the determination-result information storage 123, pieces of information (data ID) that identify respective target images may be stored in association with result IDs. For example, in the determination-result information storage 123, dates and hours at which respective target images are detected (captured) may be stored in association with result IDs.

Returning to FIG. 3, explanation is continued. For example, a Central Processing Unit (CPU), a Graphics Processing Unit (GPU), or the like executes, by using a RAM and the like as a work region, a program (for example, determination program according to the present disclosure, etc.) stored in the excrement judgement device 100 so as to realize the control unit 130. The control unit 130 is a controller, and is realized by an integrated circuit such as an Application Specific Integrated Circuit (ASIC) and a Field Programmable Gate Array (FPGA).

As illustrated in FIG. 3, the control unit 130 includes an acquisition unit 131, a determination unit 132, a generation unit 133, and a transmitting unit 134 so as to realize or execute function and working of information processing to be mentioned later. Note that an inner configuration of the control unit 130 is not limited to one illustrated in FIG. 3, and may be another configuration as long as being capable of executing information processing to be mentioned later.

The acquisition unit 131 acquires various kinds of information. The acquisition unit 131 acquires various kinds of information from the storage 120. The acquisition unit 131 receives various kinds of information from a device such as the sensor device 50 and the display device 10. The acquisition unit 131 receives sensor information of the sensor device 50 from the sensor device 50. The acquisition unit 131 receives request information indicating a request for information to be displayed from the display device 10.

The acquisition unit 131 acquires image information on an image obtained by capturing excrement excreted at a defecation action per time. The acquisition unit 131 receives an image obtained by capturing excrement excreted at a defecation action per time by a target person from the sensor device 50 that has captured the image. The acquisition unit 131 receives an image that is captured after a target person performs a defecation action and before the target person flushes the toilet from the sensor device 50 having captured the image.

The determination unit 132 identifies or determines various kinds of information so as to estimate various kinds of information. The determination unit 132 executes processing by using a model stored in the model information storage 121. The determination unit 132 estimates various kinds of information by using a model for executing outputting, in accordance with an input based on sensor information of the sensor device 50. The determination unit 132 receives an input of an image of a stool of a target person that is captured by the sensor device 50, and further estimates various kinds of information by using a model for executing outputting corresponding to the image.

The determination unit 132 executes processing by using sensor information of the sensor device 50 that has detected excrement of a target person and the models M1 to M3 stored in the model information storage 121. The determination unit 132 identifies a stool included in image information so as to determine properties of a plurality of stools and stool amounts corresponding to the properties of the plurality of stools. The determination unit 132 determines properties of a plurality of stools excreted by a target person and stool amounts corresponding to the properties of the plurality of stools by using output result of the models M1 to M3 to which information based on an image of the sensor device 50 having captured excrement of a target person is input.

The determination unit 132 generates input data for a model by using an image captured by the sensor device 50 or processing result by the determination unit 132. For example, the determination unit 132 inputs an image captured by the sensor device 50 to the model M1 so as to generate information (region information) indicating a stool region identified by the model M1.

For example, the determination unit 132 determines a property of stool of a region indicated by region information by using information (region information) indicating a stool region identified by the model M1, an image captured by the sensor device 50, and the model M2 that determines a property of stool. For example, the determination unit 132 determines an amount of stool in a region indicated by region information by using information (region information) indicating a stool region identified by the model M1, an image captured by the sensor device 50, and the model M3 that determines an amount of stool.

The determination unit 132 executes a calculation process for calculating various kinds of information. In a case where there presents a plurality of stools having the same property among a plurality of stools, the determination unit 132 calculates a total value of stool amounts of the stools having the same property. The determination unit 132 calculates a representative value of a property of stool on the basis of properties of a plurality of stools at a defecation action per time. The determination unit 132 calculates a representative value of a property of stool on the basis of a ratio of a stool amount corresponding to a property of each stool to a total amount of stool amounts at a defecation action per time.

The generation unit 133 generates various kinds of information on the basis of information acquired by the acquisition unit 131. The generation unit 133 generates information by using a determination result from the determination unit 132. The generation unit 133 generates information by using a calculation result calculated by the determination unit 132. The generation unit 133 generates information by using a total value of stool amounts of stools having the same property, which is calculated by the determination unit 132. The generation unit 133 generates information by using a representative value of a property of stool which is calculated by the determination unit 132.

The generation unit 133 generates various kinds of information by appropriately using various technologies, such as a screen (image information) to be output (transmitted) to an external information processing device. The generation unit 133 generates a screen (image information) and the like to be output to the display device 10. For example, the generation unit 133 generates a screen (image information) and the like to be output to the display device 10 on the basis of information stored in the storage 120.

The generation unit 133 generates a content to be provided to the display device 10. In the example illustrated in FIG. 1, the generation unit 133 generates the content CT1. The generation unit 133 generates a content CT2 exemplified in FIG. 11. The generation unit 133 generates contents CT11 and CT12 exemplified in FIG. 12. The generation unit 133 generates contents CT21 and CT22 exemplified in FIG. 13.

The generation unit 133 may generate a screen (image information) and the like by any process as long as being capable of generating a screen (image information) and the like to be output to an external information processing device. For example, the generation unit 133 generates a screen (image information) to be output to the display device 10 by appropriately using various technologies related to image generation, image processing, etc. For example, the generation unit 133 generates a screen (image information) to be output to the display device 10 by appropriately using various technologies such as Java (Registered Trademark). Moreover, the generation unit 133 may generate a screen (image information) to be output to the display device 10 on the basis of a format such as Cascading Style Sheets (CSS), JavaScript (Registered Trademark), and Hyper Text Markup Language (HTML). For example, the generation unit 133 may generate a screen (image information) by using various formats such as Joint Photographic Experts Group (JPEG), Graphics Interchange Format (GIF), and Portable Network Graphics (PNG).

The transmitting unit 134 functions as an outputting unit that outputs various kinds of information. The transmitting unit 134 transmits information to an external information processing device. For example, the transmitting unit 134 transmits various kinds of information to a device such as the sensor device 50 and the display device 10.

The transmitting unit 134 associates properties of a plurality of stools and stool amounts corresponding to the properties of the plurality of stools with each other, which are determined by the determination unit 132, and further outputs it to a device to be displayed such as the display device 10. For example, the transmitting unit 134 transmits, to the display device 10, properties of a plurality of stools and stool amounts corresponding to the properties of the plurality of stools that are determined by the sensor device 50 and/or the determination unit 132 in association with each other.

In a case where there presents a plurality of stools having the same property among a plurality of stools, the transmitting unit 134 outputs a total value of stool amounts of the stools having the same property. The transmitting unit 134 outputs a representative value of a property of stool on the basis of properties of the plurality of stools at a defecation action per time. The transmitting unit 134 outputs a representative value of a property of stool on the basis of a ratio of a stool amount corresponding to a property of each stool to a total amount of stool amounts at a defecation action per time.

The transmitting unit 134 transmits, to the display device 10, information determined by the determination unit 132. The transmitting unit 134 transmits, to the display device 10, information generated by the generation unit 133. In the example illustrated in FIG. 1, the transmitting unit 134 transmits the content CT1 to the display device 10.

<4-2. Functional Configuration of Display Device>

Next, a functional configuration of the display device 10, which is one example of the device, will be explained with reference to FIG. 8. FIG. 8 is a block diagram illustrating one example of a configuration of the display device according to the embodiment.

As illustrated in FIG. 8, the display device 10 includes a communication unit 11, an input unit 12, a display 13, a storage 14, a control unit 15, and a sound outputting unit 16.

The communication unit 11 is realized by, for example, an NIC, a communication circuit, or the like. The communication unit 11 is connected to the network N (Internet, etc.) in a wired or wireless manner so as to transmit and receive information to and from another device such as the excrement judgement device 100.

The input unit 12 receives various operations from a person (may be referred to as "operator") that operates the display device 10. Various kinds of information is input to the input unit 12 via the display 13. The input unit 12 has function of detecting sound. For example, the input unit 12 includes a keyboard and/or a mouse connected to the display device 10. The input unit 12 may include a button provided to the display device 10 and/or a microphone that detects sound.

For example, the input unit 12 may include a touch panel capable of realizing functions similar to those of a keyboard and/or a mouse. In this case, the input unit 12 receives various operations from an operator via a display screen by using functions of a touch panel that is realized by various sensors. In other words, the input unit 12 receives various operations from an operator via the display 13 of the display device 10. For example, the input unit 12 receives an operation, such as an operator specifying operation, via the display 13 of the display device 10. For example, the input unit 12 functions as a reception unit that receives an operation of an operator by using functions of a touch panel. In this case, the input unit 12 and a reception unit 153 may be integrated with each other. In a tablet terminal, a detection method of an operation of an operator in the input unit 12 mainly employs electrostatic capacity, another detection method of a resistance-film type, a surface-acoustic-wave type, an infrared-ray type, an electromagnetic-induction type, or the like may be employed as long as being capable of detecting an operation of an operator so as to realize functions of a touch panel.

The display 13 provided to the display device 10 displays various kinds of information. The display 13 is realized by, for example, a liquid crystal display, an organic Electro-Luminescence (EL) display, or the like. The display 13 may be realized by any device as long as being capable of displaying information that is output from the excrement judgement device 100. The display 13 displays various kinds of information in accordance with control executed by a display controlling unit 152.

In the example illustrated in FIG. 1, the display 13 displays the content CT1. The display 13 displays the content CT2 that is exemplified in FIG. 11. The display 13 displays the contents CT11 and CT12 that are exemplified in FIG. 12. The display 13 displays the contents CT21 and CT22 that are exemplified in FIG. 13. For example, the display device 10 executes a program (displaying program) for displaying information so as to display information on the display 13.

The storage 14 is realized by a semiconductor memory element such as a RAM and a flash memory, or a storage such as a hard disk and an optical disk. The storage 14 stores therein various kinds of information in displaying information. The storage 14 stores therein various kinds of information such as a displaying program.

For example, a CPU, an MPU, or the like executes, by using a RAM and the like as a work region, a program (for example, displaying program according to the present disclosure, etc.) stored in the display device 10 so as to realize the control unit 15. The control unit 15 is a controller, and may be realized by an integrated circuit such as an ASIC and an FPGA.

As illustrated in FIG. 8, the control unit 15 includes an acquisition unit 151, the display controlling unit 152, the reception unit 153, and a transmitting unit 154 so as to realize or execute function and working of information processing to be mentioned later. Note that an inner configuration of the control unit 15 is not limited to one illustrated in FIG. 8, and may be another configuration as long as being capable of executing information processing to be mentioned later.

The acquisition unit 151 acquires various kinds of information. The acquisition unit 151 acquires various kinds of information from the storage 14. The acquisition unit 151 receives various kinds of information from another information processing device such as the excrement judgement device 100.

The acquisition unit 151 receives, from the excrement judgement device 100, information obtained by associating properties of a plurality of stools and stool amounts corresponding to the properties of the plurality of stools with each other. The acquisition unit 151 receives a content from the excrement judgement device 100. In the example illustrated in FIG. 1, the acquisition unit 151 receives the content CT1.

The display controlling unit 152 controls displaying of various kinds of information. The display controlling unit 152 controls displaying of the display 13. The display controlling unit 152 controls displaying of the display 13 on the basis of information received by the acquisition unit 151. The display controlling unit 152 controls displaying of the display 13 on the basis of information received by the reception unit 153. The display controlling unit 152 controls displaying of the display 13 such that the content CT1 is displayed on the display 13.

The reception unit 153 receives various kinds of information. For example, the reception unit 153 receives an input from an operator via the input unit 12. The reception unit 153 receives an operation of an operator. The reception unit 153 receives an operation of an operator with respect to information displayed on the display 13. The reception unit 153 receives utterance by an operator as an input.

The transmitting unit 154 transmits various kinds of information to an external information processing device. For example, the transmitting unit 154 transmits various kinds of information to another information processing device such as the display device 10. The transmitting unit 154 transmits information stored in the storage 14.

The sound outputting unit 16 outputs various kinds of information as sound. For example, the sound outputting unit 16 includes a speaker that outputs sound. The sound outputting unit 16 outputs information to an operator with the use of sound. The sound outputting unit 16 outputs information displayed on the display 13 with the use of sound. For example, the sound outputting unit 16 outputs information included in the content CT1 with the use of sound.

Note that the display device 10 may realize, by using predetermined application, the above-mentioned processes for displaying and receiving an operation by the display 13. The display device 10 may acquire a script to be executed in predetermined software application so as to execute, by using control information such as the acquired script, the above-mentioned information processing for displaying information and receiving an operation, etc. For example, the control information corresponds to a program for realizing information processing such as displaying information and receiving an operation executed by the display device 10 according to the embodiment, and is realized by, for example, CSS, JavaScript (Registered Trademark), HTML, or an arbitrary language that is capable of describing the above-mentioned information processing for displaying information and receiving an operation by the display device 10. In a case where the above-mentioned display controlling process and/or receiving process are executed by dedicated application, the control unit 15 may include an application controlling unit that controls predetermined application (for example, web browser, etc.) and dedicated application, for example.

The display device 10 may receive, from the excrement judgement device 100, information obtained by associating properties of a plurality of stools and stool amounts corresponding to the properties of the plurality of stools with each other; generate a content by using information obtained by associating the received properties of a plurality of stools and the stool amounts corresponding to the properties of the plurality of stools with each other; and display the generated content. In this case, the display device 10 may include a generation unit having functions similar to those of the generation unit 133 (see FIG. 4).

<5. Flow of Processing>

Figure 9:
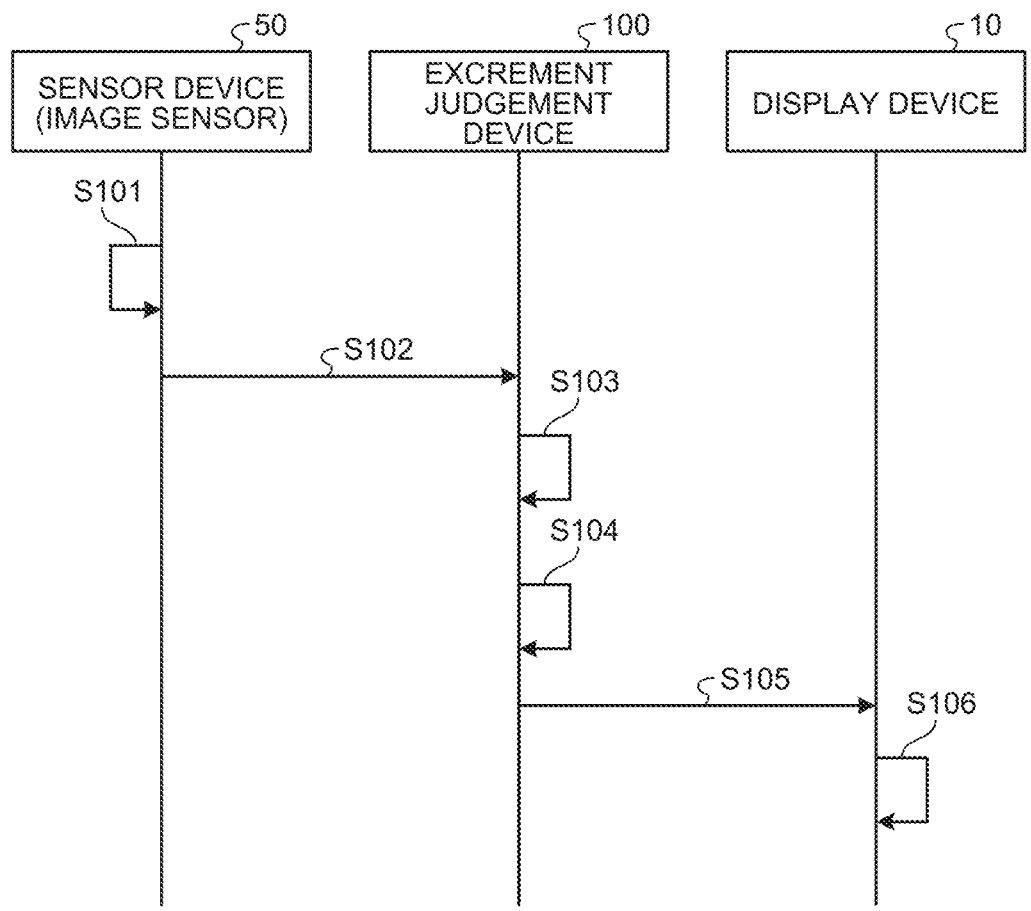
FIG. 9 is a sequence diagram illustrating one example the excrement judgement process according to the embodiment.
Figure 10:
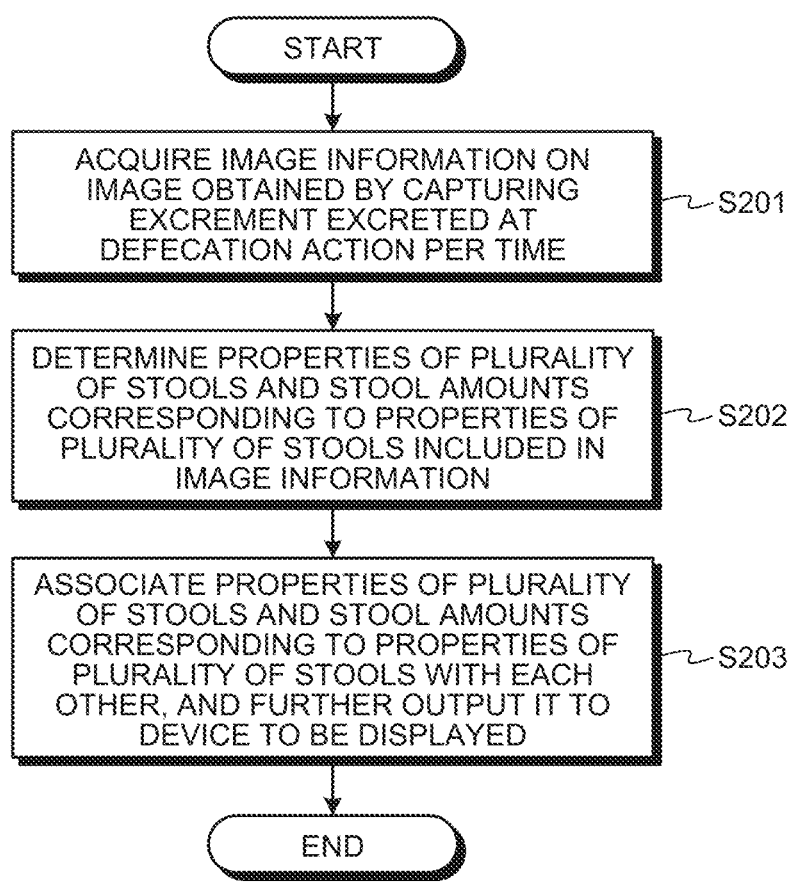
FIG. 10 is a flowchart illustrating one example of a procedure for an excrement judgement system process.

Hereinafter, flow of the processing according to the embodiment will be explained with reference to FIGS. 9 and 10.

<5-1. Processing Sequence>

Next, a processing sequence of the excrement judgement system 1 will be explained with reference to FIG. 9. FIG. 9 is a sequence diagram illustrating one example the excrement judgement process according to the embodiment.

First, the sensor device 50 detects a stool excreted by a target person (Step S101). For example, the sensor device 50 detects (captures) an image of a water sealing part in the closet bowl CB of the toilet TL.

The sensor device 50 transmits, to the excrement judgement device 100, sensor information indicating the detected stool of the target person (Step S102). For example, the sensor device 50 transmits, to the excrement judgement device 100, the captured image of the stool of the target person.

The excrement judgement device 100 having received sensor information from the sensor device 50 executes a determination process (Step S103). For example, the excrement judgement device 100 executes a determination process by using the captured image of the stool of the target person. The excrement judgement device 100 executes the determination process by using artificial intelligence (AI), in other words a model learned by machine learning. The excrement judgement device 100 inputs, to the model, an image received from the sensor device 50, and further determines a stool of a target person on the basis of an output from the model.

The excrement judgement device 100 generates a content on the basis of a determination result (Step S104). The excrement judgement device 100 generates, on the basis of the determination result, a content obtained by associating properties of a plurality of stools and stool amounts corresponding to the properties of the plurality of stools with each other. For example, the excrement judgement device 100 generates, by using the determination result, a content to be output to the display device 10 that is a device capable of displaying information.

The excrement judgement device 100 outputs the generated content to the display device 10 that is a device capable of displaying information (Step S105). The excrement judgement device 100 outputs the generated content to the display device 10 used by a manager that executes health management on a target person. For example, the excrement judgement device 100 transmits a content to the display device 10.

The display device 10 having received a content displays the content (Step S106). The display device 10 displays the content obtained by associating properties of a plurality of stools and stool amounts corresponding to the properties of the plurality of stools with each other. For example, the display device 10 used by a manager that executes health management on a target person displays a content indicating a determination result of stool of the target person.

<5-2. Processing Procedure of Excrement Judgement Process>

First, a processing procedure of the excrement judgement process will be explained with reference to FIG. 10. FIG. 10 is a flowchart illustrating one example of a processing procedure to be executed by the excrement judgement system.

The excrement judgement system 1 acquires image information on an image obtained by capturing excrement excreted at a defecation action per time (Step S201). For example, the excrement judgement device 100 of the excrement judgement system 1 acquires image information on an image obtained by capturing excrement excreted at a defecation action per time.

The excrement judgement system 1 determines properties of a plurality of stools and stool amounts corresponding to the properties of the plurality of stools included in the image information (Step S202). For example, the excrement judgement device 100 of the excrement judgement system 1 determines properties of a plurality of stools and stool amounts corresponding to the properties of the plurality of stools included in the image information.

The excrement judgement system 1 associates properties of a plurality of stools and stool amounts corresponding to the properties of the plurality of stools with each other, and further outputs it to a device to be displayed (Step S203). For example, the excrement judgement device 100 of the excrement judgement system 1 associates properties of a plurality of stools and stool amounts corresponding to the properties of the plurality of stools with each other, and further outputs it to a device to be displayed. The excrement judgement device 100 associates properties of a plurality of stools and stool amounts corresponding to the properties of the plurality of stools with each other, and transmits it to the display device 10.

<6. Other Displaying Examples>

Figure 11:
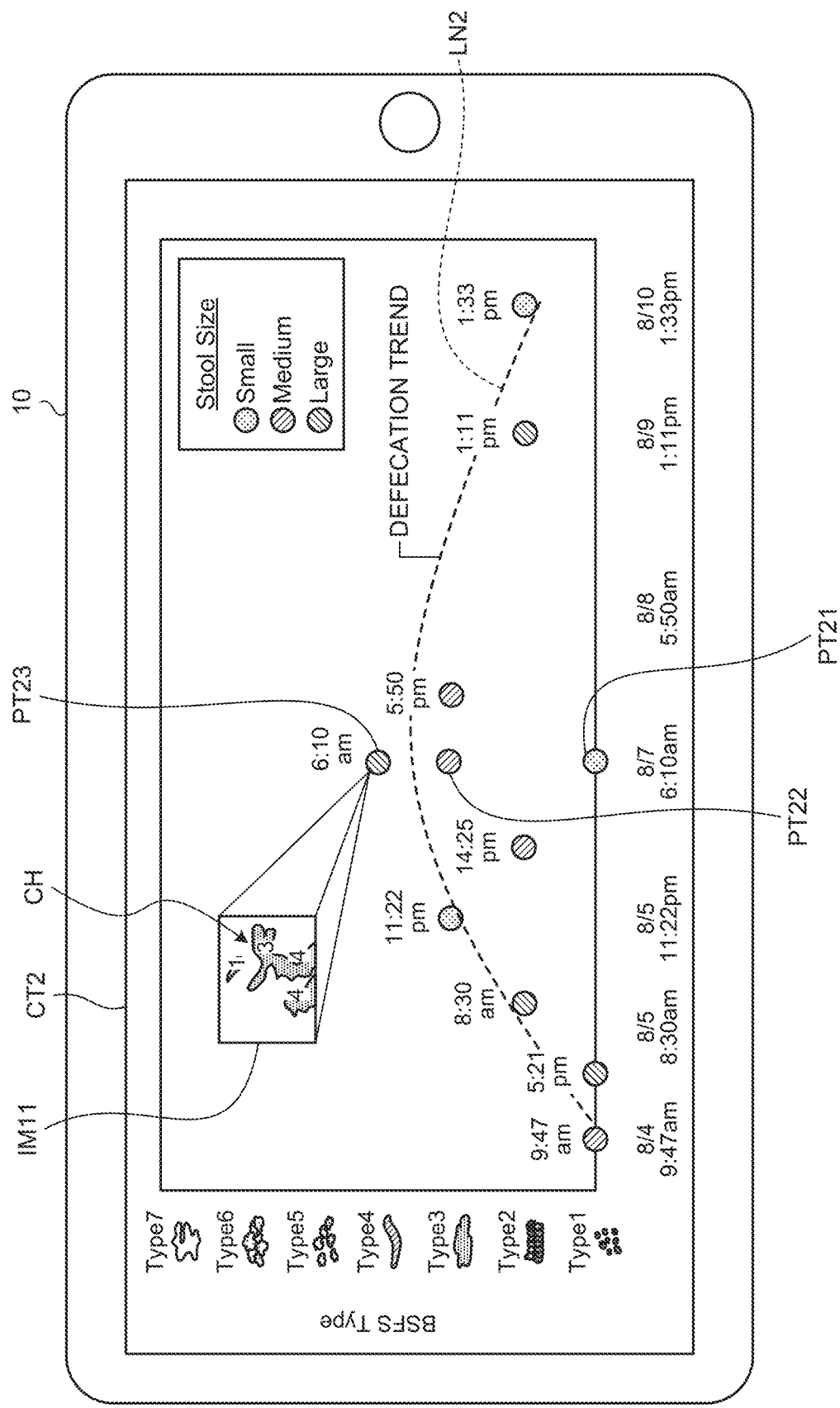
FIG. 11 is a diagram illustrating another displaying example of information related to the excrement judgement.

The displaying illustrated in FIG. 2 is merely one example, and information may be displayed in various modes. For example, displaying of a stool amount may be displayed in another mode. One example of this point will be explained with reference to FIG. 11. FIG. 11 is a diagram illustrating another displaying example of information related to the excrement judgement. Note that a part similar to the content having explained with reference to FIG. 2 and the like is provided with the same reference symbol to appropriately omit duplicated explanation. For example, a stool identification determination process and processes for generating a content and the like in the excrement judgement device 100 are common to those in explanation with reference to FIG. 2, and thus hereinafter, difference in a displaying mode alone will be mainly explained and detailed explanation of processing in the excrement judgement device 100 is appropriately omitted.

A displaying example of information will be explained with reference to FIG. 11. For example, the content CT2 illustrated in FIG. 11 is displayed on a screen of the display device 10 such as a terminal device of a manager (healthcare worker, etc.) that checks a defecation record. Explanation with respect to features of the content CT2 illustrated in FIG. 11 that are common to those of the content CT1 is appropriately omitted.

The excrement judgement device 100 generates the content CT2 that indicates in time series information obtained by associating properties of a plurality of stools and stool amounts corresponding to the properties of the plurality of stools with each other with respect to the user U1. For example, the excrement judgement device 100 generates the content CT2 including a graph that expresses an amount (size) of a stool by using a color of a plotted point (circle), and a lateral axis (X-axis) corresponds to time series and a vertical axis (Y-axis) corresponds to a property of stool. Note that in FIG. 11, difference between colors of plotted circles is expressed by using difference between hatching manners; however, in an actual displaying, each circle has corresponding color that is corresponding to hatching provided thereto.

For example, a dot-hatched circle indicates that an amount (size) is "Small (small)", and in an actual displaying, a circle whose amount (size) is "Small (small)" is displayed in red. For example, a hatched circle with diagonal hatching lines extending from the upper left to the lower right indicates that an amount (size) is "Medium (medium)", and in an actual displaying, a circle whose amount (size) is "Medium (medium)" is displayed in green. For example, a hatched circle with diagonal hatching lines extending from the upper right to the lower left indicates that an amount (size) is "Large (large)", and in an actual displaying, a circle whose amount (size) is "Large (large)" is displayed in blue. For example, with respect to an amount (size), a case where a length is 3 cm to 4 cm may correspond to "Small (small)", a case where a length is 6.5 cm to 10 cm may correspond to "Medium (medium)", and a case where a length is equal to or more than 10 cm may correspond to "Large (large)". In this case, a case where a length is 4 cm to 6.5 cm may correspond to "Medium (medium)", for example.

In FIG. 11, the excrement judgement device 100 generates the content CT2 indicating that a defecation action per time of the user U1 corresponding to 6:10 on August 7th includes a stool whose stool property is Type1, a stool whose stool property is Type3, and a stool whose stool property is Type4. For example, the excrement judgement device 100 determines, by using the image IM11, that a defecation action per time of the user U1 corresponding to 6:10 on August 7th includes a stool whose stool property is Type1, a stool whose stool property is Type3, and a stool whose stool property is Type4. The excrement judgement device 100 determines, by using the image IM11, that an amount of Type1-stool at 6:10 on August 7th is small. The excrement judgement device 100 determines, by using the image IM11, that an amount of Type3-stool at 6:10 on August 7th is middle. The excrement judgement device 100 determines, by using the image IM11, that an amount of Type4-stool at 6:10 on August 7th is large.

The excrement judgement device 100 generates the content CT2 obtained by associating a plurality of properties of stools with stool amounts corresponding to the respective properties. The excrement judgement device 100 generates the content CT2 that includes a plurality of circles having shapes PT21 to PT23 corresponding to respective stool properties as indicated in a region AR1, with respect to a defecation action per time of the user U1 corresponding to 6:10 on August 7th. The excrement judgement device 100 generates the content CT2 in which the shape PT21 whose stool property corresponds to Type1-stool, the shape PT22 whose stool property corresponds to Type3-stool, and the shape PT23 whose stool property corresponds to Type4-stool are arranged in a part corresponding to 6:10 on August 7th.

In FIG. 11, the excrement judgement device 100 generates the content CT2 that expresses a stool amount corresponding to a property for each of a plurality of properties of stools by using a color of a circle. An amount of Type1-stool at 6:10 on August 7th is small, and thus the excrement judgement device 100 generates the content CT2 that expresses the shape PT21 corresponding to Type1-stool by using a color corresponding to a stool amount "small". An amount of Type3-stool at 6:10 on August 7th is middle, and thus the excrement judgement device 100 generates the content CT2 that expresses the shape PT22 corresponding to Type3-stool by using a color corresponding to a stool amount "middle". An amount of Type4-stool at 6:10 on August 7th is large, and thus the excrement judgement device 100 generates the content CT2 that expresses the shape PT23 corresponding to Type4-stool by using a color corresponding to a stool amount "large". Note that as described above, a mode is illustrated in FIG. 11, in which difference in color is expressed by using difference between hatching manners.

Similarly, with respect to another defecation action per time, the excrement judgement device 100 also determines properties and amounts of stool, and further generates the content CT2 expressed in a mode corresponding to the determined properties and amounts. In FIG. 11, the excrement judgement device 100 generates the content CT2 including a trend line LN2 that is information indicating a time-course tendency in defecation of the user U1 that is a target person. For example, the excrement judgement device 100 generates the content CT2 obtained by associating an image corresponding to each defecation action per time with a display position corresponding to a corresponding defecation action per time. In FIG. 11, the excrement judgement device 100 generates the content CT2 obtained by associating the image IM11 corresponding to a defecation action per time at 6:10 on August 7th with a part corresponding to 6:10 on August 7th on the lateral axis.

The excrement judgement device 100 outputs the content CT2 to the display device 10. For example, the excrement judgement device 100 transmits the content CT2 to the display device 10. The display device 10 displays the received content CT2. Thus, the display device 10 displays a plurality of stool amounts corresponding to properties of a plurality of stools included in a defecation action per time. The content CT2 illustrated in FIG. 11 indicates a state where the image IM11 is displayed; however, it is possible that the image IM is not displayed until an operator of the display device 10 specifies the displaying.

The display device 10 displays the content CT2 that displays in time series information obtained by associating properties of a plurality of stools and stool amounts corresponding to the properties of the plurality of stools with each other, with respect to the user U1. For example, the display device 10 displays the content CT2 including a graph that expresses an amount (size) of a stool by using a color of a plotted point (circle), and a lateral axis (X-axis) corresponds to time series and a vertical axis (Y-axis) corresponds to a property of stool. The display device 10 displays the content CT2 indicating that a defecation action per time corresponding to 6:10 on August 7th with respect to the user U1 includes a stool whose stool is property is Type1, a stool whose stool is property is Type3, and a stool whose stool is property is Type4.

In FIG. 11, the display device 10 displays the content CT2 including the trend line LN2 that is information indicating a time-course tendency in defecation of the user U1 that is a target person. The display device 10 displays the image IM11 when an operator of the display device 10 specifies a part (for example, region AR) corresponding to 6:10 on August 7th on the lateral axis. In this case, the display device 10 displays the image IM11 when an operator of the display device 10 clicks the region AR.

Note that in FIG. 11, when displaying the image IM11, the display device 10 displays, on the image IM11 in a superposed manner, the character information CH indicating stool properties corresponding to respective stools in the image IM11. In FIG. 11, when displaying the image IM11, the display device 10 displays, on the image IM11 in a superposed manner, "1" for a region of stool whose property is Type1, "3" for a region of stool whose property is Type3, and "4" for a region of stool whose property is Type4.

<7. Total Value>

Figure 12:
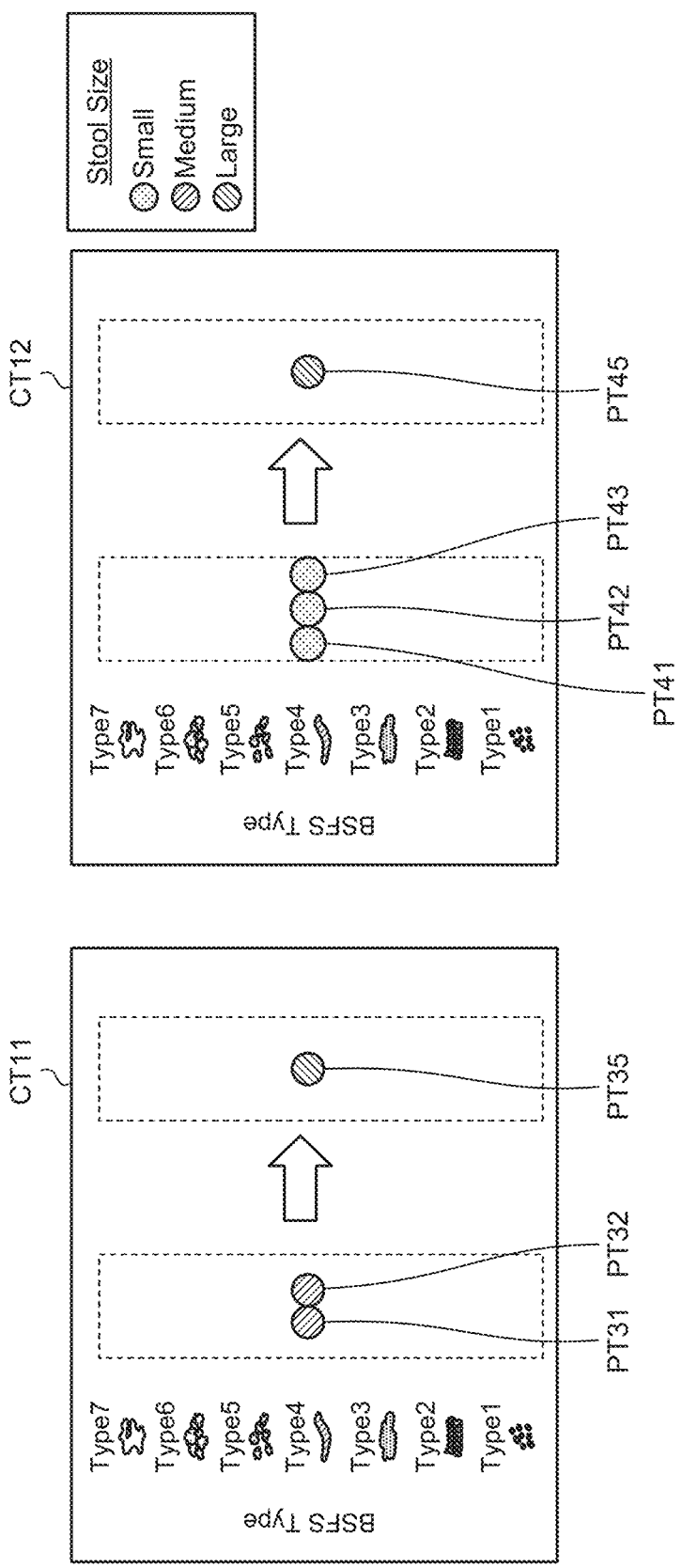
FIG. 12 is a diagram illustrating one example of displaying based on a total value.

The above-mentioned processes are merely examples, and the excrement judgement system 1 may use various values. One example of this point will be described below. First, a total value and a displaying example thereof will be explained with reference to FIG. 12. FIG. 12 is a diagram illustrating one example of displaying based on a total value.

For example, as indicated in a content CT11, in a case where there presents a plurality of stools having the same property in a defecation action per time, the excrement judgement system 1 may display a total value amount (size) of the stools. In this case, in a case where there presents a plurality of stools having property of Type4 and whose stool amount is "Medium (medium)" in a defecation action per time, the excrement judgement system 1 may totalize amounts of the plurality of stools, and display it, for example. For example, as indicated in the content CT11, the excrement judgement system 1 may totalize a shape PT31 and a shape PT32 corresponding to stools having property of Type4 and whose stool amounts are "Medium (medium)", and further may display it as a shape PT35. In this case, the excrement judgement system 1 may display the shape PT35 corresponding to stools having property of Type4 and whose stool amounts are "Large (large)" instead of the shape PT31 and the shape PT32.

For example, in a case where there presents a plurality of stools having the same property in a defecation action per time, the excrement judgement device 100 may add up amounts (sizes) of the stools having the same property, and further calculate a total value of amounts of the stools having the same property. In the content CT11 illustrated in FIG. 12, there present two stools having a common property of Type4 in a defecation action per time, the excrement judgement device 100 adds up stool amounts "Medium (medium)" of the two stools so as to calculate that an amount of stool having a property of Type4 is "Large (large)". The excrement judgement device 100 generates a content (hereinafter, may be referred to as "content CT3") that includes the shape PT35 indicating that a total value of an amount of stool having a property of Type4 is "Large (large)".

The excrement judgement device 100 outputs the content CT3 including the shape PT35 to the display device 10. For example, the excrement judgement device 100 transmits the content CT3 to the display device 10. The display device 10 displays the received content CT3. Thus, in a case where there presents a plurality of stools having the same property among a plurality of stools included in a defecation action per time, the display device 10 displays a content in a displaying mode corresponding to a total value obtained by totalizing amounts of the plurality of stools.

Similarly, as indicated in a content CT12, in a case where there presents a plurality of stools having the same property in a defecation action per time, the excrement judgement system 1 may display a total value of amounts (sizes) of the stools. Explanation of a part common to the explanation of the content CT11 is appropriately omitted. For example, as indicated in the content CT12, the excrement judgement system 1 may totalize a shape PT41, a shape PT42, and a shape PT43 corresponding to stools having a property of Type4 and whose stool amounts are "Small (small)", and display it as a shape PT45. In this case, the excrement judgement system 1 may display the shape PT45 corresponding to a stool having a property of Type4 and whose stool amount is "Large (large)" instead of the shape PT41, the shape PT42, and the shape PT43.

For example, in a case where there presents a plurality of stools having the same property in a defecation action per time, the excrement judgement device 100 may add up amounts (sizes) of the stools having the same property, and further calculate a total value of amounts of the stools having the same property. In the content CT12 illustrated in FIG. 12, there present three stools having a common property of Type4 in a defecation action per time, the excrement judgement device 100 adds up stool amounts "Small (small)" of the three stools so as to calculate that an amount of stool having a property of Type4 is "Large (large)". The excrement judgement device 100 generates a content (hereinafter, may be referred to as "content CT4") that includes the shape PT45 indicating that a total value of an amount of stool having a property of Type4 is "Large (large)".

The excrement judgement device 100 outputs the content CT4 including the shape PT45 to the display device 10. For example, the excrement judgement device 100 transmits the content CT4 to the display device 10. The display device 10 displays the received content CT4. Thus, in a case where there presents a plurality of stools having the same property among a plurality of stools included in a defecation action per time, the display device 10 displays a content in a displaying mode corresponding to a total value obtained by totalizing amounts of the plurality of stools.

<8. Representative Value>

In the above-mentioned example, stools having the same property are added up, the excrement judgement system 1 may display stools having different properties together. In this case, the excrement judgement system 1 may calculate a representative value obtained by adding up stools having different properties, and further execute displaying based on the calculated representative value. Hereinafter, a representative value and a displaying example thereof will be explained with reference to FIG. 13. FIG. 13 is a diagram illustrating one example of displaying based on a representative value.

For example, in a case where two stools have respective stool properties of Type2 and Type4, the excrement judgement device 100 may calculate that a representative value is Type3. The excrement judgement device 100 may output information indicating two stools as a stool corresponding to Type3. Regarding an amount of stool, the excrement judgement device 100 may use a total value of amounts of two stools.

For example, in a case where three stools have respective stool properties of Type2, Type4 and Type6, the excrement judgement device 100 may calculate that a representative value is Type4. The excrement judgement device 100 may output information indicating three stools as a stool corresponding to Type4.

For example, as indicated in a content CT21, the excrement judgement system 1 may display such that two stools respectively having stool properties Type2 and Type6 correspond to a representative value of Type4. For example, as indicated in the content CT21, the excrement judgement system 1 may add up a shape PT51 that corresponds to a stool whose property is Type2 and a shape PT52 that corresponds to a stool whose property is Type6 so as to display it as a shape PT55. In this case, the excrement judgement system 1 may display the shape PT55 corresponding to a stool having a property of Type4 instead of the shape PT51 and the shape PT52. In this case, the excrement judgement system 1 may display such that an amount of stool corresponding to the shape PT55 is "Large (large)".

For example, the excrement judgement device 100 may calculate a representative value of properties of a plurality of stools in a defecation action per time. In the content CT21 illustrated in FIG. 12, the excrement judgement device 100 calculates that a representative value of two stools respectively having stool properties of Type2 and Type6 is Type4. The excrement judgement device 100 generates a content (hereinafter, may be referred to as "content CT5") that includes the shape PT55 corresponding to a stool having a property of Type4.

The excrement judgement device 100 outputs the content CT5 including the shape PT55 to the display device 10. For example, the excrement judgement device 100 transmit the content CT5 to the display device 10. The display device 10 displays the received content CT5. Thus, the display device 10 displays a content in a displaying mode corresponding to a representative value of properties of a plurality of stools in a defecation action per time.

The above-mentioned processes are merely examples, and the excrement judgement system 1 may calculate a representative value in consideration of amounts (sizes) of stools having the respective Types. In this case, the excrement judgement system 1 may display a representative value of properties of a plurality of stools in a defecation action per time on the basis of a ratio of stool size.

For example, in a case where a total amount of amounts of a plurality of stools is assumed to be "100" and an amount of Type2-stool is "50" and an amount of Type6-stool is "50", the excrement judgement device 100 calculates that a representative value is Type4 (=2*0.5+6*0.5).

For example, in a case where a total amount of amounts of a plurality of stools is assumed to be "100" and an amount of Type2-stool is "75" and an amount of Type6-stool is "25", the excrement judgement device 100 calculates that a representative value is Type3 (=2*0.75+6*0.25). In a case where the calculated representative value is over a plurality of Types, the excrement judgement device 100 may output a value of the closest Type as a representative value. For example, in a case where the calculated representative value includes a decimal, the excrement judgement device 100 may execute thereon an arbitrary process such as rounding off to obtain an integer, and calculate the obtained integer as a value of Type. For example, in a case where the calculated representative value is "5.125", the excrement judgement device 100 may calculate that a representative value is Type5 by a process of rounding off. For example, in a case where the calculated representative value is "5.725", the excrement judgement device 100 may calculate that a representative value is Type6 by a process of rounding off. The above-mentioned processes are merely examples, the excrement judgement device 100 may calculate a representative value by an arbitrary process.

For example, as indicated in a content CT22, the excrement judgement system 1 may display such that a representative value of a stool having a property of "Type2" and whose amount is "small" and a stool having a property of "Type6" and whose amount is "large" is Type5. Note that a case is illustrated where a total amount of amounts of a plurality of stools is assumed to be "100" and an amount of Type2-stool is "25" and an amount of Type6-stool is "75". For example, as indicated in the content CT22, the excrement judgement system 1 may add up a shape PT61 that corresponds to a stool whose property is Type2 and a shape PT62 that corresponds to a stool whose property is Type6 so as to display it as a shape PT66. In this case, the excrement judgement system 1 may display the shape PT66 corresponding to a stool having a property of Type5 instead of the shape PT61 and the shape PT62. In this case, the excrement judgement system 1 may display such that an amount of stool corresponding to the shape PT66 is "Large (large)".

For example, the excrement judgement device 100 may calculate a representative value of properties of a plurality of stools in a defecation action per time. In the content CT22 illustrated in FIG. 12, the excrement judgement device 100 calculates that a representative value of two stools respectively having stool properties of Type2 and Type6 is Type5 (=2 0.25+6 0.75) on the basis of a ratio of stool size. The excrement judgement device 100 generates a content (hereinafter, may be referred to as "content CT6") that includes the shape PT66 corresponding to a stool having a property of Type5.

The excrement judgement device 100 outputs the content CT6 including the shape PT66 to the display device 10. For example, the excrement judgement device 100 transmits the content CT6 to the display device 10. The display device 10 displays the received content CT6. Thus, the display device 10 displays a content in a displaying mode corresponding to a representative value of properties of a plurality of stools in a defecation action per time.

The above-mentioned processes are merely examples, and in a case where not considering a ratio of stool size, as indicated in the content CT22, the excrement judgement system 1 may add up the shape PT61 and the shape PT62 so as to display it as a shape PT65 corresponding to a stool having a property of Type4.

<9. Device>

In the above-mentioned examples, the display device 10 used by a manager that executes health management on a target person is explained to be one example of a device; however, the device may be, not limited to the display device 10, any device as long as executing desired displaying. For example, as indicated in the example illustrated in FIG. 2, any device may be employed as long as having displaying function for displaying properties of a plurality of stools and stool amounts corresponding to the properties of the plurality of stools in association with each other, and the device may be a toilet operating device arranged in the toilet space PS1, for example. The device may be a user terminal such as a smartphone or a tablet terminal used by a target person (user) him/herself.

For example, the excrement judgement device 100 is connected to the toilet operating device and the user terminal via the predetermined network N (see FIG. 3) in a wired or wireless manner to be able to execute transmission and reception of information. The excrement judgement device 100 transmits information obtained by associating properties of a plurality of stools and stool amounts corresponding to the properties of the plurality of stools with each other to a toilet operating device and a user terminal.

<10. Authentication>

As described above, the excrement judgement system 1 may execute personal authentication for specifying a target person (user) having performed excretion.

For example, in the example illustrated in FIG. 1, personal authentication is executed by using a device (may be referred to as "toilet operating device") that is arranged in the toilet space PS1 so as to receive various operations related to a toilet from a user. In this case, the excrement judgement system 1 executes personal authentication by using a toilet operating device arranged in the toilet space PS1. For example, the toilet operating device may be a remote controller for changing intensity and/or a position of bottom washing by a warm water flushing toilet seat. For example, the user U1 operates the toilet operating device, and the excrement judgement device 100 receives, from the toilet operating device, information indicating that a person that uses the toilet space PS1 is the user U1.

In this case, the toilet operating device arranged in the toilet space PS1 functions as an authentication device. For example, the toilet operating device is capable of specifying a user, and further functions as an authentication device where a user operates the toilet operating device and specifies the user so as to execute personal authentication. In the example illustrated in FIG. 1, the user U1 operates the toilet operating device, and further specifies the user U1 so as to execute his/her personal authentication.

In a case where the toilet operating device is a terminal device such as a tablet terminal including a display screen, a user specifies the user from among a user group displayed on the toilet operating device so as to execute his/her personal authentication.

In a case where a user carries a user terminal into a toilet space, the user terminal and a toilet operating device may communicate with each other so that a toilet operating device may specify the user that uses the user terminal as a user that uses the toilet space.

For example, the user terminal may be connected to the toilet operating device to be able to communicate with each other by a predetermined wireless communication function such as Bluetooth (Registered Trademark) and Wireless Fidelity (Wi-Fi: Registered Trademark). In the example illustrated in FIG. 1, the user terminal of the user U1 may perform pairing between the toilet operating device by using, for example, Bluetooth and the like so as to specify that the user U1 is a user that is using the toilet space PS1.

Personal authentication may be executed by detection result of various sensors that are arranged in the toilet space PS1. In this case, the excrement judgement device 100 is an authentication device including an authentication unit that specifies a user on the basis of detection result of various sensors in the sensor device 50. The authentication unit of the excrement judgement device 100 functions as an authentication method. For example, the excrement judgement device 100 specifies a user on the basis of detection result of a sensor in the sensor device 50 and the like. Note that the excrement judgement device 100 may use detection result of any sensor as long as being capable of personal authentication (specifying) of users.

The excrement judgement device 100 communicates with a sensor device such as the sensor device 50, and further receives information detected by the sensor device from the sensor device so as to specify a user on the basis of the information. For example, the excrement judgement device 100 may specify a user by using sensor information (image, etc.) of a sensor device including an image sensor that captures an entrance of the toilet space PS1. In this case, the excrement judgement device 100 may compare an image detected by the image sensor with an image of users stored in the storage 120 so as to specify a user that is going to use the toilet space PS1.

Note that the aforementioned is merely one example, personal authentication may be performed by any process as long as being capable of specifying (personal authentication) of a user (target person) of a toilet space.

<11. Toilet Space>

The toilet space in which the sensor device 50 is arranged is not limited to the toilet space PS1 that is a toilet arranged in a facility such as the facility for the elderly illustrated in FIG. 1; and may be a toilet space of a toilet that is provided to a house (residence). In this case, a user is able to precisely know a state of improvement in a symptom, which is obtained by taking a commercial medicine that is obtained from a pharmacy by the user him/herself. As described above, in a case where specifying (personal authentication) of a user (target person) of a toilet space is possible, a toilet space in which the sensor device 50 is arranged may be a toilet space that is placed in any location. For example, a toilet space in which the sensor device 50 may be a toilet space that is arranged in a store such as a department store, an amusement park, a stadium, an office building, a park, a parking lot, and the like.

the above-mentioned embodiments and modifications may be appropriately combined within a consistent range of processing details.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

1 Excrement judgement system
100 Excrement judgement device
110 Communication unit
120 Storage
121 Model information storage
122 Image information storage
123 Determination-result information storage
130 Control unit
131 Acquisition unit
132 Determination unit
133 Generation unit
134 Transmitting unit (Outputting unit)
10 Display device (Device)
11 Communication unit
12 Input unit
13 Display
14 Storage
15 Control unit
151 Acquisition unit
152 Display controlling unit
153 Reception unit
154 Transmitting unit
16 Sound outputting unit
PS1 Toilet space

What is claimed is:

1. An excrement judgement system comprising:
an acquisition device that acquires image information including information on a plurality of stools excreted in a defecation action;
a determination device that determines types of a defining property, which is based on stool hardness, of the plurality of stools included in the image information and stool amounts corresponding the types of the plurality of stools; and
an outputting device that outputs a content associating the types of the plurality of stools with the stool amounts to a device to be displayed,
wherein the content comprises a first association between a first type of the plurality of stools and a first stool amount and a second association between a second type of the plurality of stools and a second stool amount, and
wherein the first association and the second association each are distinctly displayed at the device.

2. The excrement judgement system according to claim 1, wherein
the outputting unit outputs, in a case where there presents two or more stools having a same type among the plurality of stools for which types are determined, a total value of the stool amounts of the two or more stools having the same type.

3. The excrement judgement system according to claim 1, wherein
the outputting unit outputs, based on the types of the plurality of stools in the defecation action, a representative value of the types of the stools.

4. An excrement judgement system comprising:
an acquisition unit that acquires image information including information on a plurality of stools excreted in a defecation action;
a determination unit that determines types of a defining property, which is based on stool hardness, of the plurality of stools included in the image information and stool amounts corresponding the types of the plurality of stools; and
an outputting unit that associates the types of the plurality of stools with the stool amounts corresponding to the types and outputs the associated types and the stool amounts to a device to be displayed,
wherein the outputting unit outputs, for a stool, a representative value of a type, of the types, of the stool, and
wherein the representative value of the type is based on a ratio of a stool amount, of the stool amounts, corresponding to the type, to a total amount of the stool amounts in the defecation action.

5. An excrement judgement method comprising:
acquiring image information including information on the plurality of stools excreted in a defecation action;
determining types of a defining property, which is based on stool hardness, of the plurality of stools included in the image information and stool amounts corresponding to the types of the plurality of stools; and
associating the types of the plurality of stools and the stool amounts corresponding to the types of the plurality of stools; and
outputting a content associated the types of the plurality of stools and the stool amounts to a device to be displayed,
wherein the content comprises a first association between a first type of the plurality of stools and a first stool amount and a second association between a second type of the plurality of stools and a second stool amount, and
wherein the first association and the second association each are distinctly displayed at the device.

6. An excrement judgement device comprising:
an acquisition unit that acquires image information including information on a plurality of stools excreted in a defecation action;
a determination unit that determines types of a defining property, which is based on stool hardness, of the plurality of stools included in the image information and stool amounts corresponding to the types of the plurality of stools; and
an outputting unit that outputs a content associating the types of the plurality of stools and the stool amounts to a device to be displayed,
wherein the content comprises a first association between a first type of the plurality of stools and a first stool amount and a second association between a second type of the plurality of stools and a second stool amount, and
wherein the first association and the second association each are distinctly displayed at the device.

* * * * *